(12) United States Patent
Vossmeyer et al.

(10) Patent No.: US 7,253,004 B2
(45) Date of Patent: Aug. 7, 2007

(54) CHEMICAL SENSORS FROM NANOPARTICLE/DENDRIMER COMPOSITE MATERIALS

(75) Inventors: Tobias Vossmeyer, Fellbach (DE); Akio Yasuda, Stuttgart (DE); Roland E. Bauer, Mainz (DE); Klaus Müllen, Köln (DE)

(73) Assignee: Sony Deutschland GmbH, Koeln (DE)

( * ) Notice: Subject to any disclaimer, the term of this patent is extended or adjusted under 35 U.S.C. 154(b) by 698 days.

(21) Appl. No.: 10/197,905

(22) Filed: Jul. 18, 2002

(65) Prior Publication Data

US 2003/0109056 A1    Jun. 12, 2003

(30) Foreign Application Priority Data

Jul. 19, 2001    (EP)    ................... 01117463

(51) Int. Cl.
*G01N 30/00*    (2006.01)
(52) U.S. Cl. .................. 436/169; 422/68.1; 422/82.01; 422/82.02; 422/82.05
(58) Field of Classification Search ................. 422/50, 422/55, 68.1, 82.05
See application file for complete search history.

(56) References Cited

FOREIGN PATENT DOCUMENTS

| EP | 0 928 813 | 7/1999 |
|---|---|---|
| EP | 0928813 | 7/1999 |
| EP | 1 022 560 | 7/2000 |
| WO | WO 96/07487 | 3/1996 |
| WO | WO 97/39041 | 10/1997 |
| WO | WO 98/58970 | 12/1998 |
| WO | WO 99/27357 | 6/1999 |
| WO | WO 00 00808 | 1/2000 |
| WO | WO 00/33062 | 6/2000 |
| WO | WO 00 46839 | 8/2000 |
| WO | WO 01 50117 | 7/2001 |

OTHER PUBLICATIONS

G. Hadziioannou et al., "Semiconducting Polymers" Chemistry, Physics and Engineering, Wiley-VCH, Weinheim, Germany.
D. Bethell, et al. From monolayers to nanostructured materials: an organic chemist's view of self-assembly, J. Electroanal. Chem. 1996, 409, pp. 137-143.
U. M. Wiesler, et al., "Divergent Synthesis of Polyphenylene Dendrimers: The Role of Core and Branching Reagents upon Size and Shape", Macromolecules 2001, 34, pp. 187-199.
Balogh, L. (University of Michigan Center for Biologic Nanotechnology, Ann Arbor, MI 48109-0533, United States) et al: "A Revolution of Nanoscale Proportions." Chemical Innovation V 30 N 3 Mar. 2001, pp. 19-26, XP001022855.

(Continued)

*Primary Examiner*—Samuel P Siefke
(74) *Attorney, Agent, or Firm*—Oblon, Spivak, McClelland, Maier & Neustadt, P.C.

(57) ABSTRACT

The invention relates to a chemical sensor comprising a sensor film formed of a nanoparticle network in which the nanoparticles are interlinked by functionalized dendrimer molecules. The dendrimers support an efficient uptake of analyte molecules by the film material and therefore enable a high sensitivity of the sensor. In addition, the chemical nature of the dendrimers strongly determines the chemical selectivity of the sensor device. By cross-linking the components of the sensitive material the sensor displays a good mechanical stability.

21 Claims, 19 Drawing Sheets

OTHER PUBLICATIONS

M.C. Lonergan et al., Chem. Mater. 1996, 8, "Array-Based Vapor Sensing Using Chemically Sensitive, Carbon Black-Polymer Resistors," pp. 2298-2312.

B.J. Doleman et al., Anal. Chem. 1998, 70, "Quantitative Study of the Resolving Power of Arrays of Carbon Black-Polymer Composites in Various Vapor-Sensing Tasks," pp. 4177-4190.

G.A. Sotzing et al., Chem. Mater. 2000, 12, Highly Sensitive Detection and Discrimination of Biogenic Amines Utilizing Arrays of Polyaniline/Carbon Black Composite Vapor Detectors, pp. 593-595.

S.D. Evans et al., J. Mater. Chem. 2000, 10, "Vapour Sensing Using Hybrid Organic-Inorganic Nanostructured Materials," pp. 183-188.

H. Wohltjen et al., Anal. Chem. 1998, 70, "Colloidal Metal-Insulator-Metal Ensemble Chemiresistor Sensor," pp. 2856-2859.

H. Tokuhisa et al., Langmuir 1997, 13, "Interactions Between Organized, Surface-Confined Monolayers and Vapor-Phase Probe Molecules. 12. Two New Methods for Surface-Immobilization and Functionalization of Chemically Sensitive Dendrimer Surfaces," pp. 5608-5612.

K. Sooklal et al., Adv. Mater. 1998, 10, "A Blue-Emitting CDS/Dendrimer Nanocomposite," pp. 1083-1087.

V. Chechik et al., Langmuir 1999, 15, "Monolayers of Thiol-Terminated Dendrimers on the Surface of Planar and Colloidal Gold," pp. 6364-6369.

M. E. Garcia et al., Anal. Chem. 1999, 71, "Preparation and Characterization of Dendrimer-Gold Colloid Nanocomposites," 256-258.

R.M. Crooks et al., Topics in Current Chemistry, 2001, 212, "Dendrimer-Encapsulated Metals and Semiconductors: Synthesis, Characterization, and Applications," 81-135.

M. Zhao et al., J. Am. Chem. Soc., 1998, 120, "Preparation of CU Nanoclusters Within Dendrimer Templates," pp. 4877-4878.

G. Bar et al., Langmuir 1996, 12, "Dendrimer-Modified Silicon Oxide Surfaces as Platforms for the Deposition of Gold and Silver Colloid Monolayers: Preparation Method, Characterization, and Correlation Between Microstructure and Optical Properties," pp. 1172-1179.

R.M. Crooks et al., Acc. Chem. Res. 2001, 34, "Dendrimer-Encapsulated Metal Nanoparticles: Synthesis, Characterization, and Applications to Catalysis." pp. 181-190.

K. Esumi et al., Langmuir 1998, 14, "Preparation of Gold Colloids with UV Irradiation Using Dendrimers as Stabilizer," pp. 3157-3159.

M. Zhao et.al., J. Am. Chem. Soc. 1999, 121, "Preparation of Highly Impermeable Hyperbranched Polymer Thin-Film Coatings Using Dendrimers First as Building Blocks and Then as in SITU Thermosetting Agents," pp. 923-930.

B. Crone.et al., Appl. Phys. Lett. 2001, 78, "Electronic Sensing of Vapors with Organic Transistors," pp. 2229-2231.

F.L. Leibowitz et al., Anal. Chem. 1999, 71, "Structures and Properties of Nanoparticle Thin Films Formed Via a One-Step Exchange-Cross-Linking-Precipitation Route," pp. 5076-5083.

M. Brust et al., Langmuir, 1998, 14, "Self-Assembled Gold Nanoparticle Thin Films With Nonmetallic Optical and Electronic Properties," pp. 5425-5429.

R.G. Nuzzo et al., J. Am. Chem. Soc. 1983, 105, "Adsorption of Bifunctional Organic Disulfides on Gold Surfaces," pp. 4481-4483.

F. Morgenroth et al., J. Mater. Chem. 1997, 7, "Nanosized Polyphenylene Dendrimers Based Upon Pentaphenylbenzene Units," pp. 1207-1211.

C.J. Hawker et al., J. Chem. Soc. Perkin Tran. 1, 1993, "Unimolecular Micelles and Globular Amphiphiles: Dendritic Macromolecules as Novel Recyclable Solubilization Agents," pp. 1287-1297.

D.V. Leff et al., Langmuir 1996, 12, "Synthesis and Characterization of Hydrophobic, Organically-Soluble Gold Nanocrystals Functionalized With Primary Amines," pp. 4723-4730.

T. Vossmeyer, et al., Chem. Int. Ed. Engl. 1997, 36, "Light-Directed Assembly of Nanoparticles," p. 1080.

M.D. Musick et al., Chem. Mater. 2000, 12, "Metal Films Prepared by Stepwise Assembly. 2. Construction and Characterization of Colloidal Au and Ag Mutlilayers," pp. 2869-2881.

M. Brust et al., Advanced Material, 1995, 7, "Novel Gold-Dithiol Nano-Networks with Non-Metallic Electronic Properties," pp. 795-797.

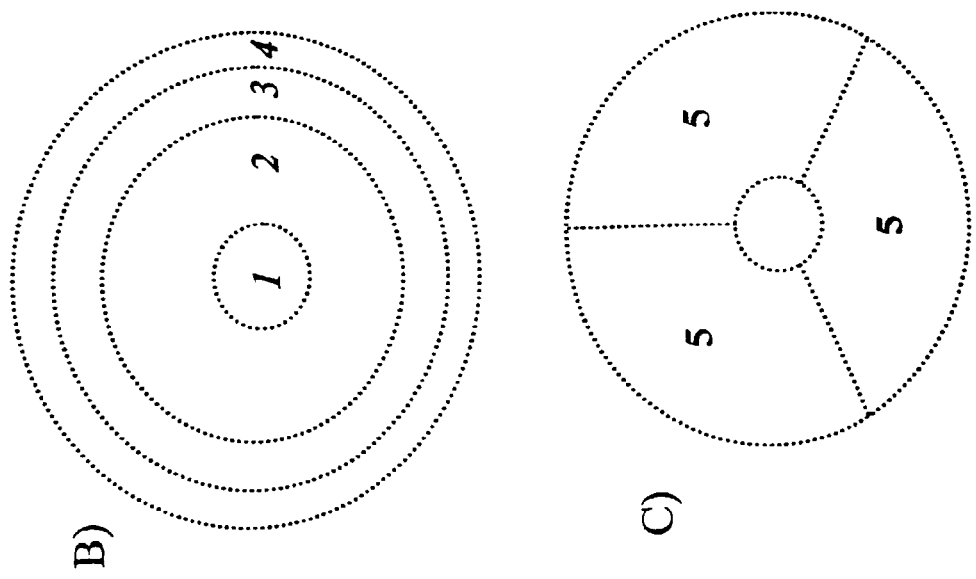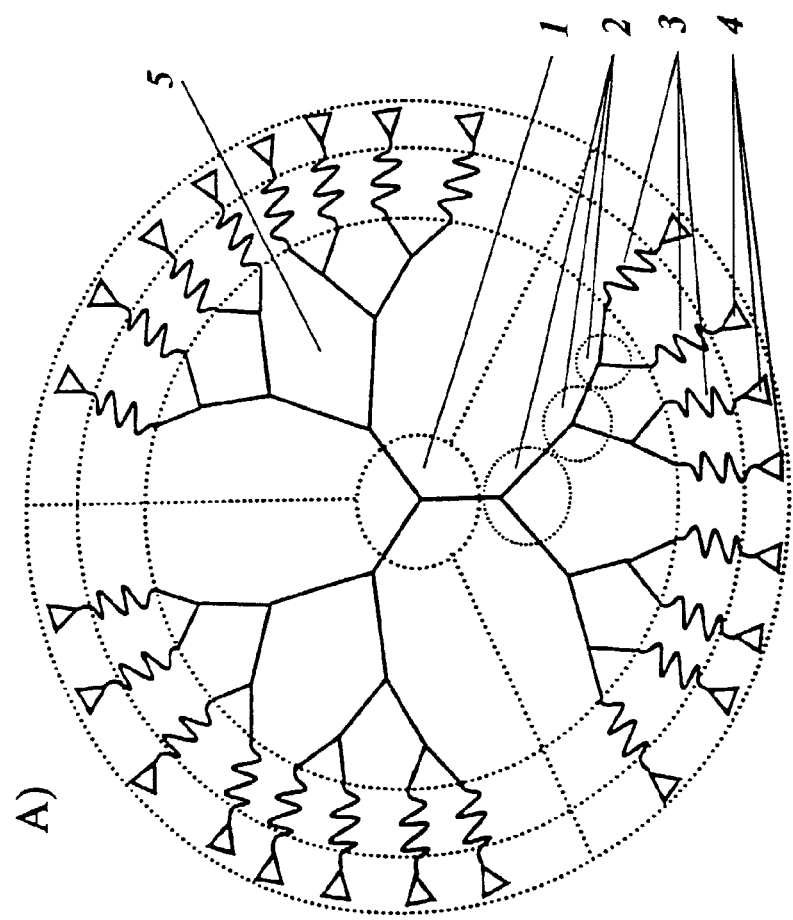
Fig.1

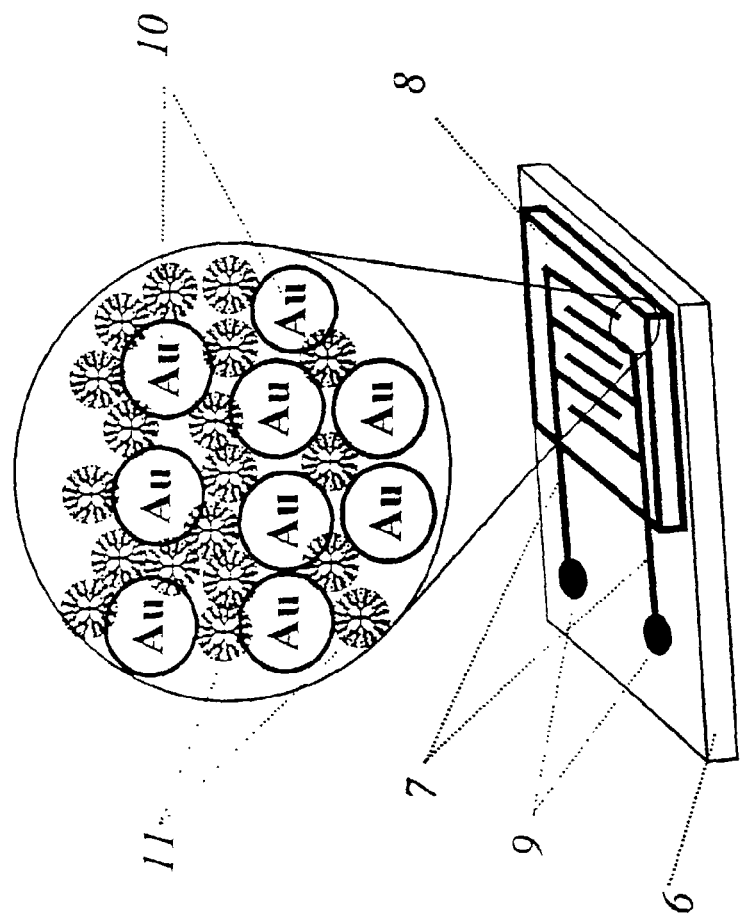

CHEMICAL SENSORS FROM NANOPARTICLE/DENDRIMER COMPOSITE MATERIALS

DESCRIPTION

The invention relates to a chemical sensor, a method for obtaining such chemical sensor and a method for detecting an analyte by using said chemical sensor.

In recent years much effort has been made to develop devices, which mimic the sense of smell or taste. Such devices, which are usually called electronic noses and electronic tongues, respectively, would be well suited for a broad variety of applications, such as entertainment robots, identification systems, quality control systems, environmental monitoring, and medical diagnostics. However, up to now only a limited number of electronic nose devices have been marketed. Although these devices are capable of identifying or classifying some "odor" samples, further improvements are necessary to fulfil the needs for many advanced applications mentioned above. These applications often require higher sensitivity, higher discrimination capability, faster response, better stability, and lower power consumption. Since such features strongly depend on the characteristics of the chemical sensors used in the device, there is a strong demand for improved sensors meeting the requirements for advanced e-nose and e-tongue applications.

During the past few years new kinds of chemical sensors have been developed based on organic/inorganic composite materials. In general these materials consist of an organic matrix comprising inorganic particulate material. The organic matrix usually determines the chemical properties of the material. Therefore, the chemical selectivity of the sensor device can be controlled by the proper functionalization of the organic matrix. The inorganic, particulate material renders some physical properties to the composite material, which change upon interaction with the analyte, and which, therefore, can be utilized for signal transduction.

M. C. Lonergan et al., *Chem. Mater.* 1996, 8, 2298-2312, describe chemically sensitive carbon black polymer resistors. Carbon black-organic polymer composites swell reversibly upon exposure to vapors. To obtain a sensor, thin films of carbon black-organic polymer composites were deposited across two metallic leads. Swelling of the film by absorption of vapors induced a change in resistance of the films and signaled the presence of an analyte. To identify and classify vapors, arrays of such vapor-sensing elements were constructed, with each element containing the same carbon black conducting phase but a different organic polymer as the insulating phase. The different gas-solid partition coefficients for the various polymers of the sensor array produced a pattern of resistance changes that can be used to classify vapors and vapor mixtures. This type of sensor array can resolve common organic solvents, including molecules of different classes such as aromatics from alcohols, as well as those within a particular class such as benzene from toluene and methanol from ethanol (see also B. J. Doleman et al., *Anal. Chem.* 1998, 70, 4177-4190).

G. A. Sotzing et al., *Chem. Mater.* 2000, 12, 593-595, describe a polyaniline-carbon black chemiresistive detector which can be used to highly sensitive detect and discriminate biogenic amines. Electrically conductive polyaniline is used as the polymeric phase of a carbon black polyaniline composite. Sorption of an odorant into the polymeric phase of the composite produces a characteristic increase in the direct current electrical resistance response of the detector. The response of the detector is approximately six orders of magnitude greater to butylamine than to water, acetone, methanol, ethylacetate, and butanol.

A drawback of the above-described sensors is that, due to the polymeric nature of the sensing material and the rather undefined dispersion of the carbon black particles, it is difficult to control structural features of the material with molecular scale precision. However, the precise control over structural parameters such as inter-particle spacing, position of the analyte-interaction sites relative to the particles, and porosity is highly desirable since this may allow to strongly enhance the sensor's properties as, for example, the chemical sensitivity or the response and recovery times. Moreover, since the carbon black particles may tend to aggregate the composite material may comprise extended regions of high and low conductivity. The size of such regions limits the possibility of device miniaturization. Also the preparation of very thin, homogenous films (<100 nm), which is desirable for enabling short response times may be difficult to achieve.

To overcome such shortcomings ligand-stabilized metal nanoparticles can be used for fabricating chemiresistor films. In this case the ligand shell surrounding the metal cores of the particles provide the organic matrix, which separates the particles from one another. Therefore the inter-particle distance can be precisely controlled through the size of the ligands. Also the molecular structure and the chemical functionality of the ligands can be utilized to tune the electronic transport properties as well as the chemical nature of the composite film. Since the ligand is linked to the nanoparticle surface, the chemical functionality, which serves as the analyte-interaction site, can be precisely positioned with respect to the nanoparticle's surface. Another advantage is that ligand-stabilized nanoparticles can easily be prepared by wet-chemical methods from various metals and with various sizes. This feature can also be exploited to further tune the physical and chemical properties of the films.

S. D. Evans et al., *J. Mater. Chem.* 2000, 8, 183-188, use para-substituted thiophenol derivatives to stabilize gold nanoparticles. The nature of the substituent group is important for controlling the relative strength of the particle-particle and particle-solvent interactions and hence in determining the physical and chemical properties of these systems. Thin films of the particles were formed by solvent evaporation on microelectrode-patterned surfaces.

The films display ohmic behavior and the room temperature conductivities vary between $10^{-6}$ and $10^{-2}$ $\Omega^{-1}$ cm$^{-1}$. Upon exposure to various chemical compounds, the thin films display a change in conductivity. The response to vapors of polar solvents display good repeatability, whereas the response to non-polar organic analytes tends to be less reproducible and displays a variety of time-dependent behavior. Depending upon the nature of the ω-functional group different conductometric and elipsometric responses to the analytes in the vapor phase are displayed. The Au-nanoparticles are not interlinked through linker molecules.

H. Wohltjen and A. W. Snow, *Anal. Chem.* 1998, 70, 2856-2859, describe a colloidal metal-insulator-metal ensemble chemiresistor sensor based on a monolayer stabilized metal nanocluster transducer film. The thin transducer film is composed of 2 nm gold clusters encapsulated by octanethiol monolayers and is deposited on an interdigitated microelectrode by air-brush technique. Upon exposure to organic vapor, large responses are displayed which are reversible. The sensor is sensitive to non-polar compounds, e.g. toluene and tetrachloroethylene, whereas little response for 1-propanol and water is displayed.

WO 00/00808 describes sensor arrays for detecting an analyte in a fluid. These arrays comprise a plurality of compositionally different sensors. The sensors comprise a conductive material embedded in a matrix of a non-conductive material, e.g. an organic polymer. As a conductive material nanoparticles might be used, that are optionally stabilized by ligand molecules attached to the central core. The ligand molecules can also be polyhomofunctionalized or polyheterofunctionalized. As an insulating material preferably organic polymers are used. It is further suggested to use an alkylthiol ligand as the sole insulating matrix.

Similar sensors and sensor arrays are described in WO 00/33062 and WO 99/08105.

A further sensor is described in FR 2783051. The sensor comprises a nanoparticle film, in which the nanoparticles are stabilized by ligand molecules with at least one functional unit to bind to the nanoparticle surface and at least one functional unit to interact with an analyte molecule.

The sensitive films of such sensors are usually fabricated by applying a solution of ligand-stabilized nanoparticles onto solid substrates and evaporating the solvent. Although the devices show promising features the fabrication of homogenous films with precise control over the film thickness is not easy to achieve by this method rendering the reproducible fabrication and miniaturization of the devices rather difficult. Moreover, the films lack mechanical stability and tend to deteriorate and detach from the substrate, especially when trying to further process the sensor substrate or when applying the sensor to liquids or under harsh environments. The lack of mechanical stability also impairs the overall sensor performance, e.g. baseline and signal stability.

To overcome such shortcomings metal nanoparticle films can be used, which are fabricated by the stepwise layer-by-layer technique described in WO 96/07487. This method is known to produce homogenous multilayered films with nanometer scale control over the average film thickness. Since this method is based on alternated and repeated self-assembly of bi- or polyfunctional linker molecules and nanoparticles the resulting film structures comprise a cross-linked nanoparticle network with greatly improved mechanical stability.

The assembly of a sensor based on self-organisation of nanoparticle-films is described in more detail in WO 99/27357. First a substrate is functionalized with 3-mercaptopropyldimethoxymethylsilane to provide binding sites for the nanoparticles. The activated substrate is then immersed in a solution that contains Au-nanoparticles, which are stabilized by a monolayer shell of alkylthiols. The thiol-groups on the surface of the substrate substitute some of the alkylthiol-ligands bound to the surface of the Au-nanoparticles, thereby attaching the nanoparticles to the surface of the substrate. By subsequently attaching alternating layers of Au-nanoparticles and linker-molecules a thin film is assembled. In the experimental part the use of 1,8-octanedithiol as a linker molecule is described. To modify the sensitivity of the sensor it is suggested to introduce heterofunctionality to the ligand shell. The ligand molecules would then be bifunctional, one functional group to bind with the metal core surface and the other to provide an attractive interaction site for sorption of the target species. It is shown, that the chemical selectivity of the sensor can be influenced by the use of differently functionalized nanoparticles. It is further shown, that the size of the nanoparticles and the thickness of the ligand shell is influencing the chemical sensitivity. The sensors, which were prepared by self-assembly, are found to be most sensitive to toluene, but less sensitive to polar analytes, e.g. propanol and water. When such sensors were exposed to relatively high concentrations of toluene vapor (ca. 2200 ppm) an increase of the resistance of up to 8.2% was reported. We investigated similar chemiresistors made from Au-nanoparticles and nonanedithiol. We observed that such sensors usually responded with a rather weak change of resistance when exposed to various vapors. For example, the relative change of resistance is below 3% when dosing such sensors with 5000 ppm toluene vapor. When applying only 5 ppm toluene vapor, the signal is usually below 0,03% and often difficult to recognize.

Besides the above described chemical sensors based on nanoparticles embedded in an organic matrix organic dentritic compounds have been used to prepare sensitive coatings for mass-sensitive chemical sensor because of their capability to take up guest molecules.

M. Wells and R. M. Crooks, *J. Am. Chem. Soc.* 1996, 118, 3988-3989 describe the immobilization of poly(amidoamine) (PAMAM) dendrimers onto a surface acoustic wave (SAW) mass balance. Voids within the dendrimer superstructure serve as endoreceptors, and the terminal functional groups of dendrimers serve as exoreceptors. When exposing the SAW-mass balances to volatile organic compounds having different functional groups, a rapid response to the dosants is obtained, wherein the response to the analytes decreases in the order acid>alcohols>hydrophobic dosants. H. Tokuhisa and R. M. Crooks, *Langmuir* 1997, 13, 5608-5612, could demonstrate, that functionalization of the outer shell of the dendrimers with different organic residues can be used to influence the chemical selectivity of the devices.

WO 97/39041 describes the fabrication of dendrimer monolayers and their application to chemical sensing. In EP 0928813 the preparation and characterization of nanostructured metal/dendrimer composite materials is described.

K. Sooklal et al., *Adv. Mater.* 1998, 10, 1083-1087 describe the preparation of CdS/dendrimer nanocomposites by the arrested precipitation of nanometer-scale CdS clusters in the presence of PAMAM-dendrimers. The optical properties of the CdS-Clusters are sensitive to synthesis conditions, including dendrimer type, solvent type, and the concentration of dendrimer and other solutes. Thin films of these CdS/dendrimer nanocomposites were prepared by casting solutions onto frosted microscope slides followed by solvent evaporation. Those thin films retain approximately the optical properties of their parent solutions. V. Chechik et al., *Langmuir* 1999, 15, 6364-6369, describe the synthesis of fourth-generation PAMAM-dendrimers having terminal groups partially or fully functionalized with thiol groups. These thiolated dendrimers form stable monolayers on planar Au-substrates. In monolayers of partially functionalized dendrimers most of the thiol groups directly interact with the Au surface. Thiol-modified dendrimers also act as efficient stabilizers for Au-nanoparticles. The particles obtained are small (1-2 nm) even when the reduction is carried out in the presence of an excess of the Au-salt. Such nanocomposites are stable and can be isolated in a pure form by gel filtration.

M. E. Garcia, L. A. Baker, R. M. Crooks, *Anal. Chem.* 1999, 71, 256-258, describe the preparation and characterization of dendrimer-gold colloid nanocomposites. Au colloids in the 2-3 nm size regime can be prepared by in situ reduction of $HAuCl_4$ in the presence of poly(amidoamine) (PAMAM) dendrimers. The dendrimers encapsulate the colloids, imparting stability to the aqueous colloidal solutions. The nanocomposite materials can be isolated by precipitation. The size of the resultant colloids is controlled by the dendrimer generation: lower generation dendrimers give rise to larger colloids.

Compared to mass sensitive chemical sensors, signal transduction and signal readout of chemiresistors is simpler and allows for easier device miniaturization and integration, especially when aiming for integration of extended sensor arrays into silicon based circuits.

It therefore is an object of the invention to provide a chemical sensor with selectivity towards target analytes, high sensitivity, simple and robust signal transduction, and high stability in performance.

To solve this object, the present invention provides a chemical sensor, comprising a substrate, a sensor medium formed on the substrate, and detection means for detecting a change of a physical property of the sensor medium, wherein the sensor medium comprises a network formed of non-linear polymer or oligomer molecules having linker units and of particles of at least one second component, wherein the linker units are bound to the surface of the particles of the at least one second component thereby interlinking said particles.

As non-linear polymer or oligomer molecules might be used star-polymers, comb-polymers, hyperbranched polymers and dendrimers. Star polymers are polymers having a more or less spherical shape provided with several arms. To a core are linked linear polymers, which spread radially outward. Comb-polymers have a linear backbone, which is formed as a linear polymer. To the backbone are connected linear polymers which spread sidewards from the molecule backbone and form side-chains. Hyperbranched polymers have a structure similar to the polymers described above but the polymers connected to the core or the backbone of the molecule are branched. The linker units form part of the polymers and are preferably situated at the terminating end of the polymer chain.

Best suited to carry out the invention are dendrimer molecules. In the following the invention will be discussed in more detail with reference to dendrimer molecules. But a chemical sensor according to the invention might also be assembled on the basis of the other non-linear polymers or oligomers mentioned above.

The chemical sensor according to the invention provides a sensor device with high sensitivity and good mechanical stability, achieved by cross-linking the components of the sensor medium with functionalized dendrimers. The use of dendrimers, which provide sites of interaction with analyte molecules, also enables tuning the chemical sensitivity through proper functionalization of the dendrimer structure. The size and structure of the dendrimer component can also be used to control the porosity of the film material. Cross-linking of the sensor medium components enables the precise control of the sensor medium architecture, e.g. the film thickness and interparticle spacings, during sensor fabrication, which improves the reproducibility of device fabrication. To obtain a fast response and a high sensitivity the sensor medium is generally formed on the substrate as a film having a thickness of around ten nanometres to few micrometers.

Dendrimers are quasi-spherical organic polymers or oligomers that have well-defined structures with less dense interiors and densely packed surfaces, especially in the case of higher generation dendrimers. General information on the physical and chemical properties and the structures of dendrimers may be found in G. R. Newkome, C. N. Moorefiled, F. Voegtle, "Dentritic Molecules: Concepts, Synthesis, Perspectives", VCH, 1996, Weinheim, Germany. The preparation and characterization of nanoparticle/dendrimer composite materials has been described e.g. in R. M. Crooks, B. I. Lemon III, L. Sun, I. K. Yeung, M. Zhao, Top. Curr. Chem. 2001, 212, 81-135; M. Zhao, L. Sun, R. M. Crooks, J. Am. Chem. Soc. 1998, 120, 4877-4878; K. Sooklal, L. H. Hanus, H. J. Ploehn, C. J. Murphy, Adv. Mater. 1998, 10, 1083-1087; G. Bar, S. Rubin, R. W. Cutts, T. N. Taylor, T. A. J. Zawodzinski, Langmuir 1996, 12, 1172-1179; R. M. Crooks, M. Zhao, L. Sun, V. Chechik, I. K. Yeung, Acc. Chem. Res. 2001, 34, 181-190; M. E. Garcia, L. A. Baker, R. M. Crooks, Anal. Chem. 1999, 71, 256-258; V. Chechik, R. M. Crooks, Langmuir 1999, 15, 6364-6369; K. Esumi, A. Suzuki, N. Aihara, K. Usui, K. Torigoe, Langmuir 1998, 14, 3157-3159; and EP 0 928 813.

Depending on the structure of the molecules different types of dendrimers, dendrons or dentritic compounds are known. All these compounds may be used for assembling a chemical sensor according to the invention and are generally called "dendrimers" or "dendrimer molecules" in the following.

The dendrimer component fulfils one of the following functions or properties or any combination thereof:

a) Molecularly designed porosity of the nanoparticle film, which enables the uptake and diffusion of analyte within the composite material. This can be utilized to improve the sensor's sensitivity and response time and to tune the selectivity of the sensor device by providing a size-selective filter effect.

b) Cross-linking other components of the composite (such as nanoparticles, oligomers, polymers) to give mechanical stability;

c) Tuning the chemical nature of the composite material and, thereby, the chemical selectivity of the intended sensor device by utilizing the chemical properties of the dendrimer's interior and/or of its surface;

d) The dendrimer may also provide some physical properties that can be used for signal transduction (e.g. luminescence, absorbance).

With respect to the invention, the dendrimer structure may be roughly divided into four parts: A core (or focal point), which forms the central part, a shell of branched repeating units, another shell of spacer units, and an outer shell of linker units, which serve to cross-link other components of the composite material.

Dendrimer structures, which are either flexible or rigid and open favor the uptake of analyte molecules by the composite material and therefore can enhance the sensitivity of the sensor device. Flexible structures usually comprise a relatively high content of $sp^3$-hybridized carbon (and/or hetero) atoms and have a high degree of conformational freedom. In contrast, rigid structures usually comprise a high content of unsaturated sp- and/or $sp^2$-hybridized carbon (and/or hetero) atoms, preferably at least 40% of the carbon atoms of the core and the shell of branched repeating units are $sp^2$ and/or sp hybridized, and the degree of conformational freedom is limited (e.g. by sterical hindrance). However, rigid dendrimer structures may also be made from $sp^3$-carbon rich cage-like compounds (e.g. adamantane and ist derivatives, cyclodextrines, metal ion/crown ether complexes, metal ion/polyether complexes), or may comprise porphyrin or phthalocyanin (which may be complexed with a metal ion), or derivatives thereof. The uptake of analyte species by flexible dendrimers is accompanied by a change of the dendrimer's shape and volume, whereas rigid dendrimers do not swell when interacting with the analytes. The chemical nature of the dendrimer interior strongly determines the chemical selectivity of the composite material.

Functional groups of the interior structure, which can interact with the analyte molecules act as endo-receptor sites. In general, polar functional groups of the dendrimer's interior tune the chemical selectivity towards polar analyte molecules, whereas non-polar functional groups (or non-polar residues) favor selectivity for non-polar analytes. Tab. 1 shows structural units that are preferably used to form the core structure and the repeating units of the dendrimer. The structural units listed in the table may be used in any combination to form the core structure and the repeating units of the dendrimer.

TABLE 1

Structural units used to form the core structure and the repeating units of dendrimers

The groups displayed in the first two lines of table 1 comprise at least three valences (*) and therefore may act as branching units and as endo-receptor sites, whereas those groups having two valences (*) act as endo-receptor sites, e.g. an imino- or an azogroup, enabling selective interaction with certain analytes. A phenyl ring may carry up to 6 branches and also may carry substituents, e.g. halogen atoms, hydroxy groups, or an organic residue, such as alkyl or alkoxy groups. X represents such substituents.

The structure of the dendrimer core and the repeating units may comprise electron-donating groups, e.g. amino groups, imino groups, aromatic groups comprising hetero atoms (N, S, O), carbonyl groups, carboxy groups, ether groups, thio groups, etc., which may be used for complexing metal cations. Suitable metal cations may be main group metals, such as $Mg^{2+}$, $Ca^{2+}$, $Pb^{2+}$, etc., transition metals, such as $Mn^{2+}$, $Co^{2+}$, $Ru^{2+}$, $Fe^{2+}$, $Fe^{3+}$, $Cu^{2+}$, $Ag^+$, $Zn^{2+}$, $Cd^{2+}$, $Hg^{2+}$, $Cr^{3+}$, $Pt^{2+}$, $Au^{3+}$, $Pd^{2+}$, etc., rare earth metals, such as $Ce^{3+}$, $Eu^{3+}$, etc., which themselves can serve to form selective interaction sites for analytes, e.g. $O_2$, CO, $NH_3$, $SO_x$, $NO_x$. Examples of metallodendrimers are given in G. R. Newkome, E. He, C. N. Moorefield, *Chem. Rev.* 1999, 99, 1689-1746. Amine units may also be protonated to form a cationic interaction site.

In order to enhance the selective interaction with certain analytes the repeating units may also be functionalized with terminating structural units. The valences of the structural units, which are not involved in linking these units to the dendrimer structure may carry a hydrogen atom or a small alkyl group, e.g. a methyl or an ethyl group, a small alkoxy group, e.g. methoxy, ethoxy, or may be deprotonated to form an ionic unit. Such terminating units may also be formed from the units given in Table 3 below.

The functional and structural units of the dendrimer may be arranged in such a way, that more than one unit can interact with the same analyte. Such a concerted interaction can strongly enhance the selectivity. Moreover the interaction sites may be arranged sterically in such a way, that they enable stereo-selective sensing, e.g. of chiral compounds.

Chemically bonded to the shell of repeating units may be a shell of spacer units. These units are structural units, which mainly serve to functionalize the outer sphere of the dendrimer with terminal linker units. Examples for structural units that may be used to form the spacer units of the dendrimers are given below in table 2. These units may be used in any combination to form the spacer units.

TABLE 2

Structural units used to form the spacer units of dendrimers

*—$CH_2$—*   *—CH=CH—*   *—C≡C—*

*—⌬—*   *—CHX—*   *—CX=*

*—N=N—*   *—N=*   *—S—*

*—S(=O)—*   *—S(=O)₂—*   *—S(=O)₂—O—*

*—O—*   *—C(=O)—*   *—C(=S)—*

*—S—S—*

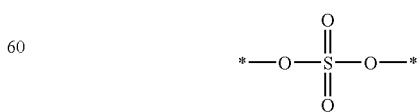

The structure of the spacer is preferably formed by alkylene, alkenylene or alkinylene groups at least comprising 3 carbon atoms. For binding the spacer to the shell of repeating units, both parts comprise suitable functional or structural groups. For example such units may form an ester linkage or an amide linkage.

The spacers carry functional groups and/or structural units at their ends that act as linker units to cross-link the dendrimers to other (second) components of the composite. Preferably the linker units are formed by polar groups and/or sulphur-containing groups. Table 3 shows preferred examples of structural units that may be used to form linker units of the dendrite molecules.

TABLE 3

Structural units used to form the linker units of dendrimers

| Structure |
|---|
| *—S—S—*   *—S—*   *—S(=O)—* |
| *—S(=O)(=O)—*   *—S(=O)(=O)—O—*   *—N(/*)\* |
| *—NC   *—P(/*)\*   *—P(=O)(—*)—* |
| *—O—P(=O)(—O—*)(—O*) |
| *—O—*   *—C(=O)—*   *—C(=S)—*   *—C(=O)—O—* |
| *—C(=O)—N(—*)—*   *—S+(/*)\*   *—N(H)—C(=S)—S—* |
| *—Si(—O—*)(—O*)—O—*   *—CH=CH—*   *—CN |

Some of the valences of the groups shown in table 3 may be terminated by a hydrogen atom thereby forming e.g. a terminating hydroxyl group, amine group or thiol group, or may be deprotonated and form for example a thiolate or carboxylate group.

The dendrimer preferably cross-links other components of the composite material through covalent bonds or coordinative bonds (e.g. metal-ligand such as Au/thiol). But linking of the dendrimer molecules may also be obtained through non-covalent bonding, such as ionic or dipole-dipole interactions or metal-ion complexation. In case the dendrimer molecules are attached to the surface of a metal particle or a semiconductor particle it is preferred, that the dendrimer molecules comprise an outer shell of suitable linker units forming the surface of the dendrimer molecule. The linker units may be coupled to the dendrimer molecule by appropriate spacer units. Preferably the linker units are selected from the group formed of thiol groups, disulfide groups, amino groups, isocyanide groups, thiocarbamate groups, dithiocarbamate groups, chelating polyether, and carboxy groups. Within the dendrimer molecule the linker units may be of the same or of different type. Polar linker units, that are not bound to the second component may also act as exo-receptors for analytes.

The structure of the dendrimer (especially the repeating units, the spacer units, and/or the linker units) may comprise or may be formed from amino acids, e.g. glycine (GLY), alanine (Ala), valine (Val), leucine (Leu), isoleucine (Ile), methionine (Met), proline (Pro), phenylalanine (Phe), tryptophan (Trp), serine (Ser), threonine (Thr), cysteine (Cys), tyrosine (Tyr), asparagine (Asn), glutamine (Gln), aspartic acid (Asp), glutamic acid (Glu), lysine (Lys), arginine (Art), histidine (His), or nucleotides, or nucleotide-building blocks, e.g. cytosine, uracil, thymine, adenine, guanine, ribose, 2-deoxyribose, or derivatives of such compounds.

If the sensing material is used for detecting non-polar analytes, the chemical nature of the dendrimer, especially the dendrimer interior structure, should also be non-polar. Preferred non-polar dendrimer structures comprise phenyl- or polyphenylene units, which are connected with each other through carbon bonds and/or ether bonds. Such dendrimers can be rather rigid and comprise defined voids in their interior, which can take up guest molecules.

If the sensing material is used for detecting polar analytes, the chemical nature of the dendrimer, especially the dendrimer interior structure, should also be polar. Because of their commercial availability a preferred dendrimer used for assembling of the sensor film is a polyamidoamine (PAMAM) dendrimer. Further preferred dendrimers that can be obtained from commercial sources are poly(propylene imine) (PPI) dendrimers. Those dendrimer molecules are available in different sizes depending on the generation of the dendrimer (e.g. generation-1 to generation-8). Those dendrimers of different generation differ in their physical and chemical properties and may therefore be used to modify the selectivity and/or sensitivity of the chemical sensor.

In both PAMAM and PPI dendrimer structures the branching positions are formed of nitrogen atoms. Also, both structures are pretty flexible, since the structural units comprise a high content of $sp^3$-hybridized atoms with a high degree of rotational freedom. Since in both cases the structure contains polar functional groups (amide- or amine-groups) these dendrimers are suited for the fabrication of sensors with selectivity for polar, hydrophilic analytes, especially the PAMAM-dendrimers, which contain hydrophilic amide groups, that can act as endo-receptors. Sensors based on PPI-dendrimers are especially selective to acidic analytes, because of the amine functional groups.

Both PAMAM- and PPI-dendrimers can incorporate (complex) metal cations (e.g. $Ag^+$, $Au^{3+}$, $Pt^{2+}$, $Pd^{2+}$, $Cu^{2+}$). Furthermore the metal cations can be reduced by UV-irradiation or by wet-chemical methods to form dendrimer stabilized metal nanoparticles. Also semiconductor materials can form clusters with such dendrimer molecules, e.g. PAMAM-stabilized CdS clusters. Nanoparticles might therefore be used as second component of the sensor medium. Stabilization of the nanoparticles by dendrimers is achieved by adsorption of the dendrimers on the nanoparticle's surface. The amino groups on the dendrimer's outer sphere serve as linker units to bind to the surface of the nanoparticles. Since the amino groups have a high affinity for many metal surfaces PAMAM-dendrimers form monolayers on metal substrates (e.g. Au substrates). Further the primary amino groups of PPI and PAMAM-dendrimers can be used to covalently attach the dendrimer to self-assembled monolayers of organic thiols, as described by Wells and Crooks (M. Wells, R. M. Crooks, *J. Am. Chem. Soc.* 1996, 118, 3988-3989).

The chemical nature of the outer sphere of PPI- and PAMAM-dendrimers can be controlled by coupling various organic residues as exo-receptors to the primary amino groups via amide coupling. This can be utilized to tune the chemical selectivity of dendrimer based sensors and/or to improve the coupling of the dendrimer molecules e.g. to the surface of a nanoparticle. This might be achieved by providing e.g. a thiol group or a disulfide group on the surface of the dendrimer molecule by coupling such linker units to the terminal amino groups through an appropriate spacer unit by an amide bond. An example, which demonstrates how PAMAM-dendrimers can be functionalized with terminal thiol groups has been described by V. Chechik et al., *Langmuir* 1999, 15, 6364-6369. Other terminal groups, which are useful to bind to many metal nanoparticles, were already given above in Table 3. PAMAM-dendrimers are also available with hydroxy termination (instead of amino termination). These dendrimers are referred to as PAMAM-OH (Sigma-Aldrich). Also carboxy-terminated PAMAM-dendrimers are commercially available. All these PAMAM-dendrimers can be used to prepare highly cross-linked dendrimer/polymer composite materials, which are useful as sensor media. The dendrimer's amino-, hydroxyl-, or carboxy-groups are utilized to cross-link the polymer components of the composite material.

Preferred is the use of dendrimer composite materials as a chemical sensor, which utilizes a change of the optical or, especially preferred, the electronic properties for signal transduction. To provide such useful optical and/or electronic properties to the composite material, nanoparticles can be used as a second component.

Nanoparticles are nanoscopic objects that are confined in at least one dimension to the nanometer scale (<1000 nm, preferably <100 nm). Thus, nanoparticles may resemble spheres (3-dimensional confinement), fibers or tubes (2-dimensional confinement) or sheets (1-dimensional confinement). Examples for 3-dimensionally confined nanoparticles are surfactant-stabilized metal and semiconductor nanoparticles, and fullerenes, such as $C_{60}$. Examples for 2-dimensionally confined nanoparticles are carbon nanotubes, and semiconductor nanofibers, such as $V_2O_5$-nanofibers. Examples for 1-dimensionally confined nanoparticles are sheets made from ZnS or titania. All those nanoparticles may be used in the assembly of the chemical sensor. Preferred is the use of three-dimensionally confined nanoparticles in the size regime between 0.8 to 100 nm.

In general nanoparticles may consist of insulating material, however for providing useful optical and/or electronical properties they preferably consist of semiconducting material, or metal. Such nanoparticles can be prepared by various methods, ranging from gas-phase techniques to wet-chemical synthesis, which have been described by numerous papers in the literature. The wet-chemical preparation methods usually provide ligand-stabilized and/or charge-stabilized nanoparticle solutions. Such preparation methods are well known to persons skilled in the art.

The nanoparticles fulfil two different tasks. First, they strongly determine the physical properties of the composite film material, which are measured when operating the sensor. If the sensing principle requires electric conductivity, then metal particles are preferred because they strongly enhance the electric conductivity of the material. This allows, for example, measuring changes of the electric conductivity as the sensor signal. As a rule of thumb, the use of larger particles leads to films with higher conductivity than using smaller ones. Moreover, many metal and semiconductor nanoparticles have pronounced optical properties (absorption and/or luminescence), which may change upon interaction of the analyte with the film material. Second, the nanoparticles serve as nanoscopic substrates for binding the dendrimer molecules. In this sense, the nanoparticles can be considered as junctions of the nanoparticle/dendrimer network. These nanoparticle networks comprise cavities in-between the nanoparticles, which support the diffusion of analyte species into the sensor film material.

It is mentioned that when using the sensor device for detecting certain target analytes, the nanoparticle material may also be used to tune the chemical selectivity of the film. For example, many metal nanoparticles can strongly interact with gases as CO, $NH_3$, $NO_x$, $SO_x$, etc. These interactions can induce strong changes of the optical and/or electronic properties, which can be used as the sensor's signal.

For the use of the nanoparticle film as a chemiresistor, an important function of the nanoparticles is to provide sufficient conductivity. Therefore, the nanoparticle preferably is a metal nanoparticle. Metals suited for the fabrication of a nanoparticle sensor film are preferably selected from the group consisting of Au, Ag, Pt, Pd, Cu, Co, Ni, Cr, Mo, Zr, Nb, and Fe. It is also possible to use nanoparticles comprising combinations (e.g. alloys) of these metals.

It is also possible to use semiconductor nanoparticles (e.g. II/VI semiconductors such as CdS, CdSe, CdTe, ZnO, ZnS, ZnSe, ZnTe, HgS, HgSe, HgTe, or III/V semiconductors such as GaAs, InAsInP, or others such as PbS, $Cd_3P_2$, $TiO_2$, $V_2O_5$, SnO and other transition metal oxides, or combinations of these materials, including core/shell structures, e.g. CdS/CdSe or CdSe/ZnS. In order to enhance the conductivity of the semiconductor nanoparticles, they may be doped (e.g. As, Sb, Al, B, P, In, Lanthanides, transition metals). In this case the dendrimers serve to interlink the nanoparticles. Semiconductor nanoparticles provide properties that can be used for optical and/or electrical signal transduction and, therefore, for the fabrication of chemical sensors.

Further, also combinations of metals, semiconductors, and/or insulators may be used as nanoparticles. As insulator materials might be used $SiO_2$, $Al_2O_3$ or MgO. Nanoparticles solely consisting of insulator materials might also be used for assembling the sensor media according to the invention.

In principle, it is also possible to provide conducting or semiconducting particles from conducting organic materials such as conducting polymers. It is understood that the nanoparticles mentioned here can also be used in any combination for preparing the sensitive materials.

In order to provide useful electronic properties to the dendrimer composite material it is also possible to combine the dendrimer component with (semi)conducting polymers or oligomers instead of (or in addition to) the above described nanoparticles. The fabrication of dendrimer/polymer composites has already been described by M. Zhao, Y. Liu, R. M. Crooks, D. E. Bergbreiter, *J. Am. Chem. Soc.* 1999, 121, 923-930, and WO/9858970. (Semi)conducting polymers or oligomers, which are useful to provide useful electronic properties to the dendrimer composite material are for example polypyrrole, polyaniline, polythiophene, or any derivatives of these polymers. Other examples of semi-conducting polymers are described in G. Hadziioannou, P. F. van Hutten (Eds.): "Semiconducting Polymers—Chemistry, Physics and Engineering", Wiley-VCH, Weinheim, Germany. Such sensor media can be fabricated by reacting the terminal functional groups of a dendrimer with functional groups of a (semi)conducting polymer (or semiconducting oligomer). Dendrimers that are suitable for this purpose may have a polar or non-polar molecular structure, tuning the chemical selectivity towards polar or non-polar analytes, respectively. The dendrimers serve to cross-link the semiconducting polymer component.

The chemical sensor according to the invention may be used in various types of chemical sensor devices that use different physical properties to detect an analyte. In a first group, a change of an electrical property is detected. For example, a change in conductivity or capacity of the sensor film may be measured. Therefore, the chemical sensor may act as a chemiresistor or a chemicapacitor. The sensor film can also be utilized in a configuration forming a chemidiode or a multiterminal device, such as a chemitransistor (e.g. Chem-FET). Examples of chemical sensitive transistors comprising semiconducting oligomers based on polythiophene have recently been described in the literature (B. Crone, A. Dodabalapur, A. Gelperin, L. Torsi, H. E. Katz, A. J. Lovinger, Z. Bao, *Appl. Phys.* Lett. 2001, 78, 2229-2231). The chemical sensor may also be used as a mass sensitive sensor. The nanoparticle film is then used as a coating on a piezo-electric material to form a chemically sensitive surface acoustic wave (SAW) device or a quartz crystal microbalance (QCM).

According to another embodiment, the chemical sensor is used as an optical sensor. The sensor signal may then be measured as a change in reflectance, fluorescence, absorption, or scattering. In this case, the binding of analyte molecules to the sensor material leads to a change of optical properties (UV/vis and/or IR). Suitable materials may comprise, for example, semiconductor nanoparticles, which show electro- and or photo-luminescence. For example, the luminescence properties may change when the analyte molecules are adsorbed to the dendrimer/nanoparticle material. This change is due to a change of the electronic states of the nanoparticles and/or of the close environment of the nanoparticles (i.e. the electronic states of the dendrimers or of the analyte itself). Examples of suitable semiconductor materials were already given above.

It is also possible to utilize the sensor films as chemically sensitive coatings for fiber optics (e.g. optodes, interferometer devices). The chemical sensor may also use changes in heat or temperature and therefore be used as a thermistor, or other thermoelectric device.

Preferably the chemical sensor is formed as a chemiresistor, wherein the sensor medium is deposited as a film on a pair of contacting electrodes.

The sensor film may be deposited onto electrodes, e.g. made of Au, which were deposited on an inert substrate, e.g. by lithographic techniques, or both electrodes may be deposited on top of the film. Also other configurations are possible. One electrode may be positioned below the sensor film and the other may be deposited on top of the sensor film. By the sorption of the analyte to the dendrimer composite material the electronic properties of the sensor are influenced resulting in a change of conductivity of the sensor film.

The inert substrate can be made for example of $Si/SiO_2$ when the chemical sensor is integrated in an IC device. Further preferred substrates are made of glass and/or ceramics.

Several chemical sensors, which preferably have different compositions of the sensor film, may be arranged to form a sensor array.

The chemical sensor according to the invention may be miniaturized, e.g. to be used in a sensor array in an IC device.

The chemical sensor comprises at least one nanoparticle and at least one dendrimer molecule.

The chemical sensor may comprise a single nanoparticle to which two dendrimer molecules are attached. The dendrimer molecules may then be attached e.g. to electrodes with a further linker unit.

According to another embodiment, the chemical sensor may comprise a single dendrimer molecule, which is attached to two nanoparticles.

The sensor film containing nanoparticles may be formed by a one-step procedure as described by F. L. Leibowitz, W. Zheng, M. M. Maye, C.-J. Zhong, *Anal. Chem.* 1999, 71, 5076-5083, who investigated the formation and properties of Au-nanoparticle/alkyldithiol films. This method is based on precipitating the film material by mixing the nanoparticles and the linker molecules in solution phase in the presence of the substrate. Thus, mixing dendrimers having suitable linker units at their surface with suitable nanoparticles results in the precipitation of a thin film composite material. However, to obtain stable nanoparticle films with high precision, the nanoparticle film is preferably prepared through layer-by-layer deposition of the nanoparticles. This procedure has been described in principle by D. Bethell, M. Brust, D. J. Schiffrin, C. Kiely, *J. Electroanal. Chem.* 1996, 409, 137-143; M. Brust, D. Bethell, C. J. Kiely, D. J. Schiffrin, *Langmuir* 1998, 14, 5424-5429, and in WO 96/07487. In the case of the present invention, the assembly of the nanoparticle film occurs through stepwise self-organization organization of the nanoparticles and of the dendrimer molecules. This allows the formation of nanoparticle sensor films under more controlled and reproducible conditions.

A further subject of the invention therefore is a method for forming a chemical sensor as described above, comprising the following steps:
  a) providing a substrate
  b) alternately depositing on the substrate a layer of nanoparticles and a layer of non-linear polymers having linker units thereby coupling the non-linear polymers to the nanoparticles until a homogenous sensor film is obtained.

Preferably dendrimer molecules are used as non-linear polymers.

Preferably the substrate is first functionalized to provide linker groups on the surface of the substrate. In a preferred embodiment the method for forming a chemical sensor comprises the following steps:
  a) functionalization of a substrate to provide linker groups on the surface of the substrate;
  b) deposition of a layer of nanoparticles on the functionalized substrate surface theeby linking the nanoparticles to the linker groups;
  c) deposition of dendrimer molecules on the layer of nanoparticles and coupling of the dendrimer molecules to the nanoparticles;
  d) deposition of a further layer of nanoparticles and linking them through the dendrimer molecules with the nanoparticles of the first layer;
  e) repeating steps c) and d) until a homogenous sensor film of nanoparticles is obtained.

The deposition of the nanoparticles and the deposition of the dendrimer molecules is repeated until a nanoparticle sensor film is obtained which has sufficient conductivity for being used as a chemiresistor (preferably R<10 MΩ). The deposition of the nanoparticles and of the dendrimer molecules may be performed by any suitable method. The nanoparticles or the dendrimer molecules may be deposited by spraying or dipping with a solution of the nanoparticles or of the dendrimer molecules in a suitable solvent and evaporation of the solvent or by a spin-coating technique. Usually the nanoparticles are applied in the form of a solution of ligand-stabilized nanoparticles. Binding of ligand or dendrimer molecules is achieved via ligand-exchange reactions. In such exchange reactions, at least some of the stabilizing ligands are exchanged by the dendrimer molecules. For example, dodecylamine ligands on the surface of Au-nanoparticles are easily exchanged by thiol functionalized dendrimer molecules. The functionalization of the substrate might be performed by e.g. coupling a mercapto- or aminoalkylsilane to the surface of the substrate.

As the last step in the formation of the sensor film preferably a layer of dendrimer molecules is depositet, so that the surface of the sensor film is formed by dendrimer molecules.

According to another embodiment of the method according to the invention the chemical sensor is produced by a method, wherein a mixture comprising non-linear polymers having linker units, nanoparticles and a solvent is prepared on the surface of a substrate or is applied to the surface of a substrate, and the solvent is removed to form a film of a sensor medium.

Also in this embodiment the surface of the substrate may first be functionalized to provide linker units on the surface of the substrate.

The above-described sensor may be used for the detection of analyte molecules in gas or solution phase. A further subject of the invention therefore is a method for detecting an analyte, wherein the sensor medium of a chemical sensor as described above is exposed to the analyte and a change of a physical property of the sensor film is measured by a detection means. The change of a physical property may be e.g. a change in conductivity, dielectric constant, reflectance, color, luminescence, absorbance, mass, volume, density, and/or heat capacity.

The invention will now be described in more detail by way of examples and with reference to the accompanying figures.

FIG. 1 shows schematically the general structure of dendrimers used for the chemical sensor of the invention;

FIG. 3 shows schematically an assembled chemiresistor;

FIG. 4b shows the size distribution of the Au-nanoparticles displayed in FIG. 4a;

Figure 10:
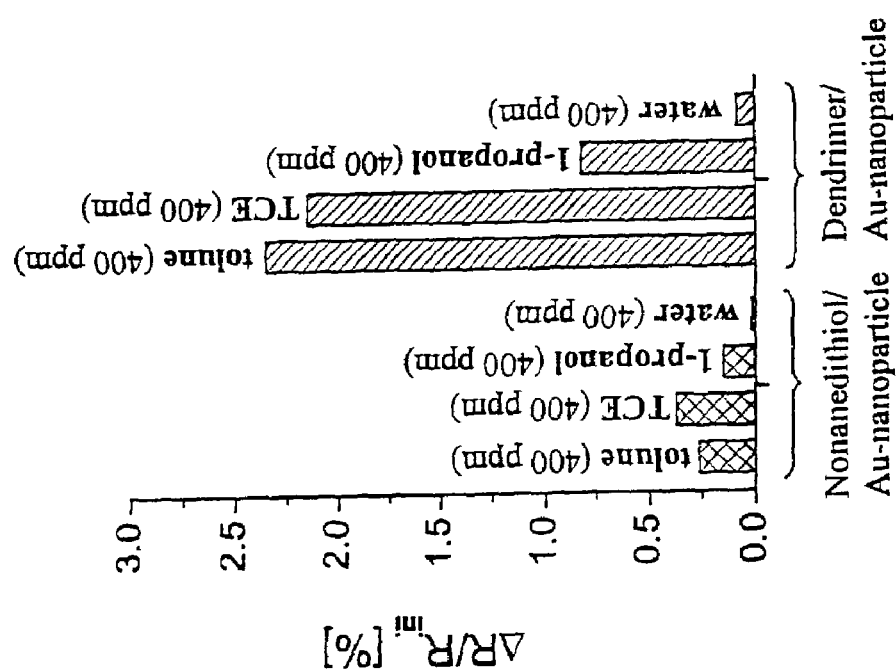
Figure 11:
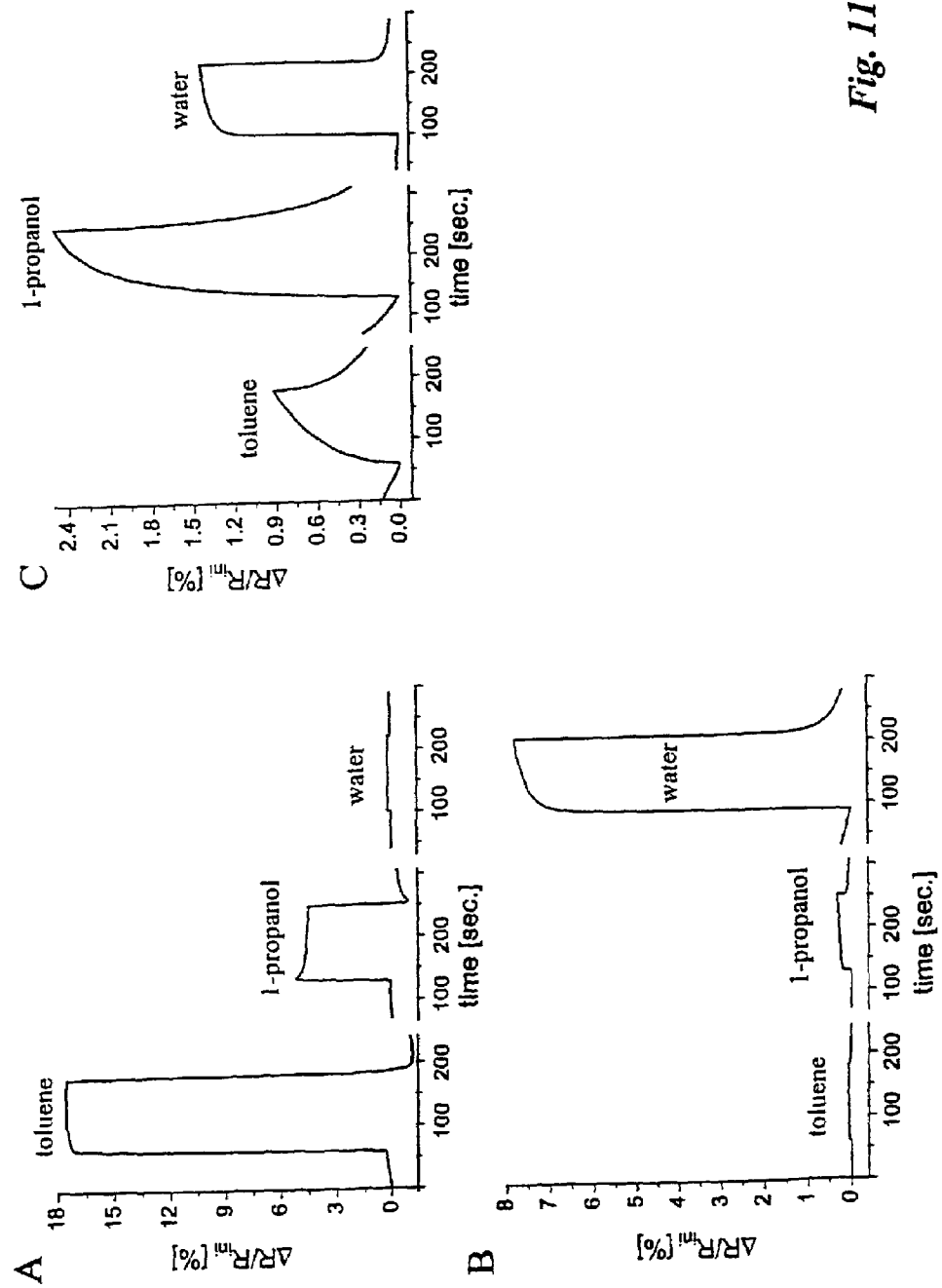

FIG. 10 is a comparison of the sensitivities measured with a polyphenylene-dendrimer/Au-nanoparticle based chemiresistor and a nonanedithiol/Au-nanoparticle based chemiresistor; and FIG. 11 shows the response curves of a polyphenylene-dendrimer/Au-nanoparticle film resistor (A), a PAMAM-dendrimer/Au-nanoparticle film resistor (B), and a PPI-dendrimer/Au-nanoparticle film resistor (C) to the exposure of 5000 ppm toluene, 1-propanol, and water.

The general structure of dendrimers, which can be used to assemble a chemical sensor according to the invention, is schematically shown in FIG. 1A. The center of the structure is the core 1 (or focal point). In the example of FIG. 1A the core has three arms (e.g. a 1,3,5-substituted phenylene ring). However, in general the core can also have a different number of arms. Preferred are cores, which have two arms (e.g. a 1,4-substituted phenyl ring or an alkylenediamine). More preferred are cores, which have three arms (e.g. a 1,3,5-substituted phenyl ring). Even more preferred are cores with four arms (e.g. carbon or silicon atoms). To each arm of the core a first "shell" of repeating units 2 is connected, each of which branches into two new arms. The atoms at the branching position of a repeating unit may be a carbon atom or a hetero atom (e.g. nitrogen). When going from the core to the outside of the structure the example shown in FIG. 1A comprises altogether three shells of repeating units. Therefore the dendrimer structure shown is called a generation-3 (G-3) dendrimer. According to the invention dendrimers of various generations can be used, however, generations 1-6 are preferred. Especially preferred are generations 1-4. Since each repeating unit shown in FIG. 1A branches into two limbs, each shell of repeating units is doubling the total number of branches. Therefore the whole number of branches at the surface of the structure is 24 (=3 (core)×2 (1. shell)×2 (2. shell)×2 (3. shell)). In general it also possible to have dendrimer structures in which each repeating unit branches into more than two limbs. According to the invention repeating units that branch into 3 limbs are preferred. More preferred are repeating units, which branch into two limbs as is shown in FIG. 1A. The repeating units may be functionalized with various chemical groups or heteroatoms to introduce endo-receptor sites into the dendrimer structure or to tune its polarity. The structure of the repeating units may be rigid or flexible. Rigid units usually comprise sp- and/or $sp^2$-hybridized carbon atoms; $sp^2$-hybridized carbon atoms may be involved in the formation of aromatic groups (e.g. phenyl rings). However, rigid dendrimer structures may also be made from $sp^3$-carbon rich cage-like compounds (e.g. adamantane and ist derivatives, cyclodextrines, metal ion/crown ether complexes, metal ion/polyether complexes), or may comprise porphyrin or phthalocyanin (which may be complexed with a metal ion), or derivatives thereof. Flexible units usually contain $sp^3$-hybridized carbon atoms (and/or hetero atoms), which enable a high degree of conformational freedom. According to the invention both flexible and rigid repeating units can be used, however, rigid repeating units are preferred. When going from the inside to the outside of the structure shown in FIG. 1A the last shell of repeating units is followed by a shell of spacer units 3. As seen in the figure, to each of the 24 branches a spacer unit is connected. These spacer units have the function to bind the linker units 4 to the outer shell of repeating units. The spacer units may comprise short linear alkylene, alkenylene, or alkinylene units with up to 16 carbon atoms, or more. In addition, the spacer units may be utilized to introduce some chemical functionalities (hetero atoms) to the dendrimer's outer structure. According to the invention both flexible or rigid spacer units may be used. However, preferred are flexible spacer units, which have a high degree of conformational freedom (e.g. which comprise alkylene chains of up to 16 carbon atoms). Other suitable units, which may be used to form the spacer structure were already given above in Tab. 2. It is mentioned that in general also dendrimers may be used, which do not comprise spacer units or in which the spacer unit is just a covalent bond. The linker units 4 are functional groups, which attach to other components of the sensor film (e.g. nanoparticles) and, thereby, cross-link the sensitive material. The linker units are arranged at the surface of the dendrimer molecules. Examples for such linker units have already been given in Tab. 3.

FIG. 1B schematically shows the spatial arrangement of the four different units, which form the dendrimer structure. In center is the core 1, which is surrounded by at least one shell of repeating units 2. The shells of repeating units are followed by a shell of spacer units 3, which at the outside of the dendrimer is surrounded by an outer shell of the linker units 4. It is noted that the shells of repeating units may be formed by chemically and structurally identical units or by chemically and/or structurally different units. The repeating units may be different from shell to shell and/or may differ within one shell. In addition, the dendrimer structure may comprise chemically and/or structurally identical or different spacer or linker units. The repeating units may be attached to the core through covalent bonds such as carbon-carbon bonds or functional bonds (e.g. ester bonds, amide bonds). Such bonds may also serve to inter-link the repeating units with each other and with the spacer units as well as the spacer units with the linker units. Coordinative bonds involving metals may also be employed to inter-link the structural units of the dendrimer.

According to the number of arms of the core 1, the dendrimer structure may be divided into segments 5 as shown in FIG. 1C. Especially, if the dendrimer is synthesized by a convergent approach, the chemical composition and/or the structural features of the segments (repeating units, the spacer units, and/or the linker units) may differ from segment to segment.

Figure 2A:
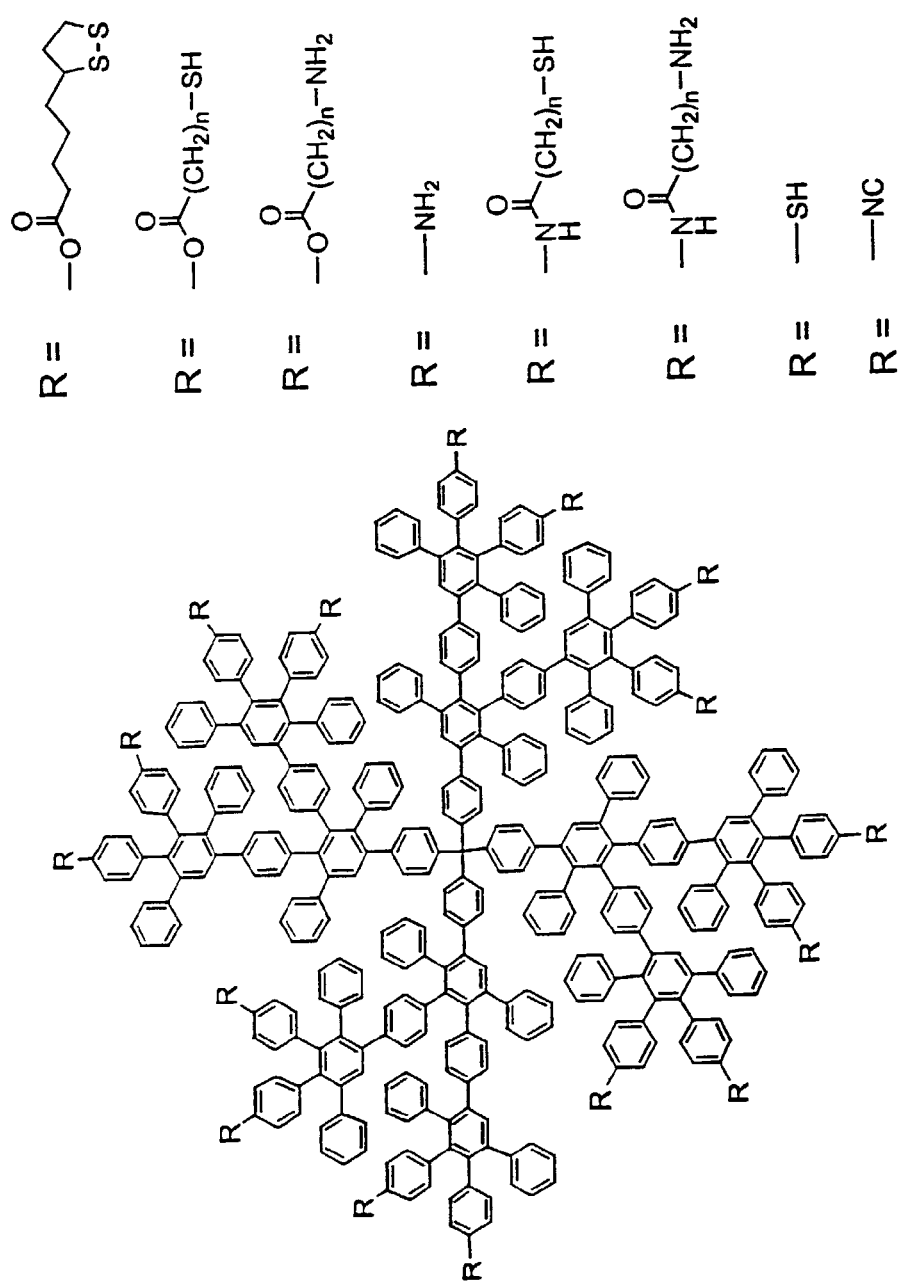
FIGS. 2a-2e show structures and structural elements of preferred dendrimers used for the chemical sensor of the invention.

A dendrimer molecule corresponding to the general description above is depicted in FIG. 2a. The core of the structure is a tetraphenylmethane unit to which four 2,3,4,5-tetraphenylbenzene repeating units are attached. To each of the tetraphenylbenzene units are two further tetraphenylbenzene units attached. This structure is therefore a generation-2 dendrimer. Each of the outer tetraphenylbenzene units carries two thioctic acid residues, which are attached through ester bonds. The thioctic acid carbon skeletons form the spacer unit shell, whereas the disulfide functional groups at the dendrimer surface form the linker unit shell. Disulfides are well known to bind to metal surfaces, such as gold surfaces as described by R. G. Nuzzo, D. L. Allara, *J. Am. Chem. Soc*. 1983, 105, 4481-4483. The dendrimer therefore is well suited to cross-link Au-nanoparticles. The polyphenylene core structure is rather rigid and has a spherical diameter of around 2.5 nm. The steric hindrance only permits a rather low degree of conformational freedom. The polyphenylene structure of the dendrimer is hydrophobic and does not contain any polar functional groups. Ester bonds serve to attach the spacer units. The sensitivity of a sensing material comprising this hydrophobic dendrimer is expected to be higher towards hydrophobic analytes than towards hydrophilic ones. The synthesis of polyphenylene type dendrimers has been described for example by F. Morgenroth, C. Kübel, K. Müllen, *J. Mater. Chem*. 1997, 7, 1207-1211, and U. -M. Wiesler, A. J. Berresheim, F. Morgenroth, G. Lieser, K. Müllen, *Macromolecules* 2001, 34, 187-199.

Figure 2B:
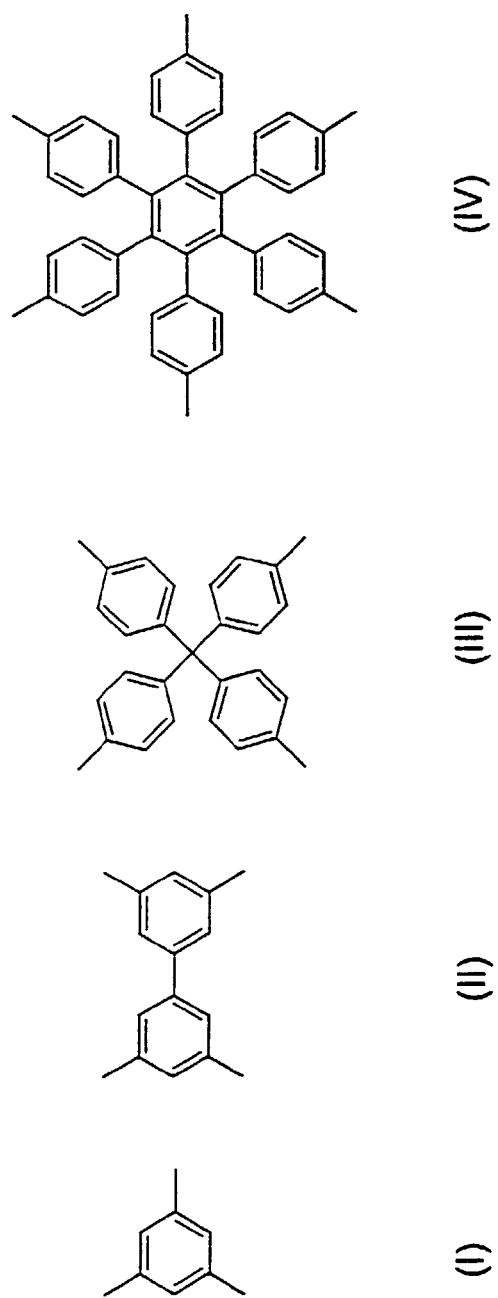

Besides the thioctic acid residues R also other spacer and/or linker units may be used. Examples of such groups are also depicted in FIG. 2a. The structure of the dendrimer shown in FIG. 2a may be modified by using a central core having three, four or six arms. Such central cores are depicted in FIG. 2b. The same repeating units, spacer units and linker units as shown for the dendrimer in FIG. 2a may be connected to the central cores of FIG. 2b.

Figure 2C:
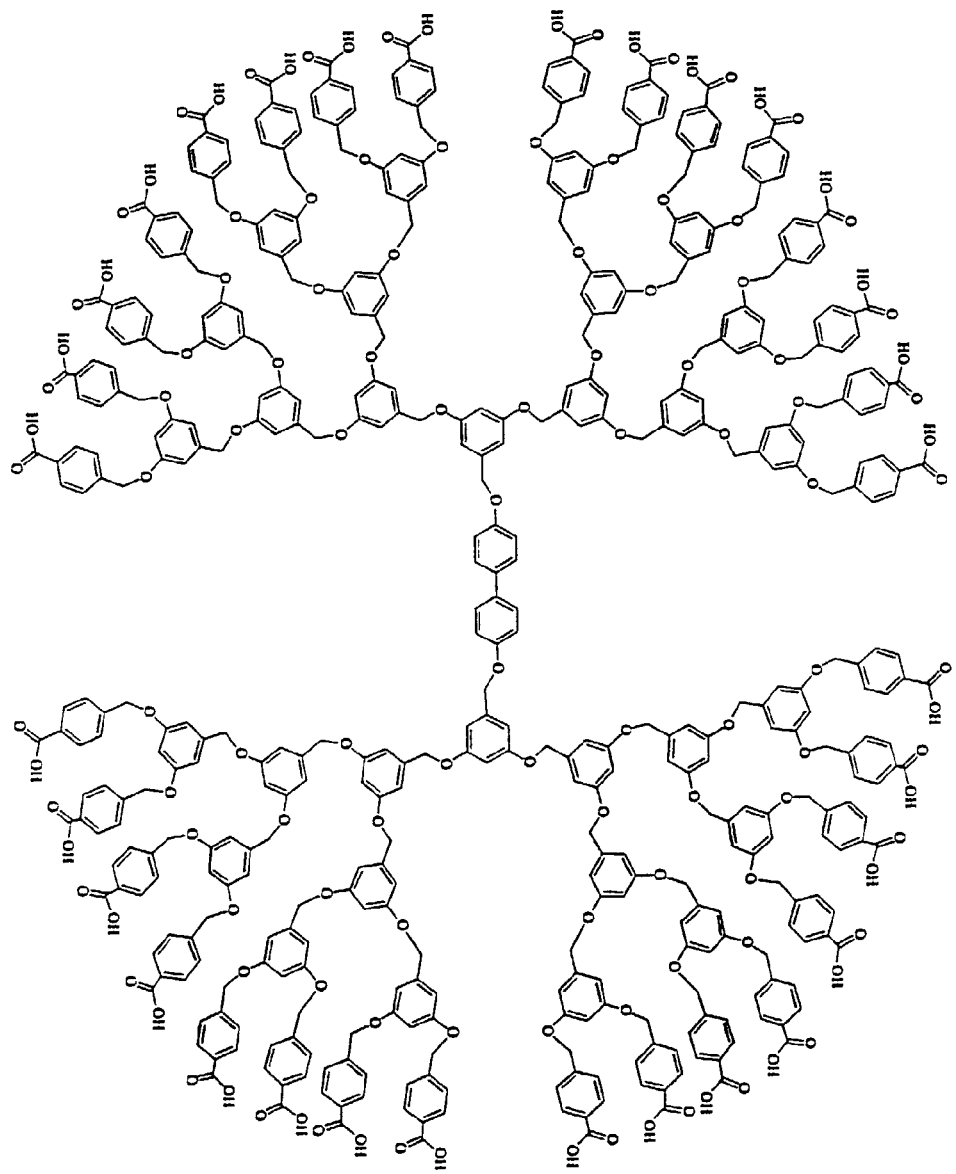

Another example of a dendrimer that can be used for assembling chemical sensors according to the invention is shown in FIG. 2c. The dendrimer molecule has been described by C. J. Hawker, K. L. Wooley, M. J. Frechet, *J. Chem. Soc. Perkin Tran*. I 1993, 1287-1297. The dendrimer also has a hydrophobic interior, but has a hydrophilic outer surface of carboxylic acid functional groups. The core of this dendrimer has two arms and consists of a 4,4'-dioxybiphenyl unit. The repeating units are derived from 3,5-hydroxybenzyl units, which are linked to each other through the oxygen atoms, thus forming a polyether macromolecular structure. Since the structure comprises four shells of repeating units, the dendrimer is a generation-4 dendrimer. The spacer units are benzyl units, to which carboxylic acid groups are attached in the para position. This structure is more flexible than the polyphenylene structure described above (FIG. 2a) because it contains $sp^3$-hybridized carbon atoms and has a higher degree of conformational freedom. The dendrimer shown in FIG. 2c has the ability to solvate hydrophobic guest molecules, such as polycyclic aromatic compounds. Sensors comprising such dendrimers therefore have pronounced selectivity for such hydrophobic analytes. The hydrophilic outer surface of carboxylic acid groups can be utilized to attach directly via covalent or non-covalent interactions to other components of the composite material of the sensor. The carboxylic acid groups can also be used to couple other functional groups to the dendrimer surface, which may be more suitable for cross-linking components of the composite material. For example, suitable linker units can be coupled to the carboxylic acid groups through ester or amide bonds.

Figure 2D:
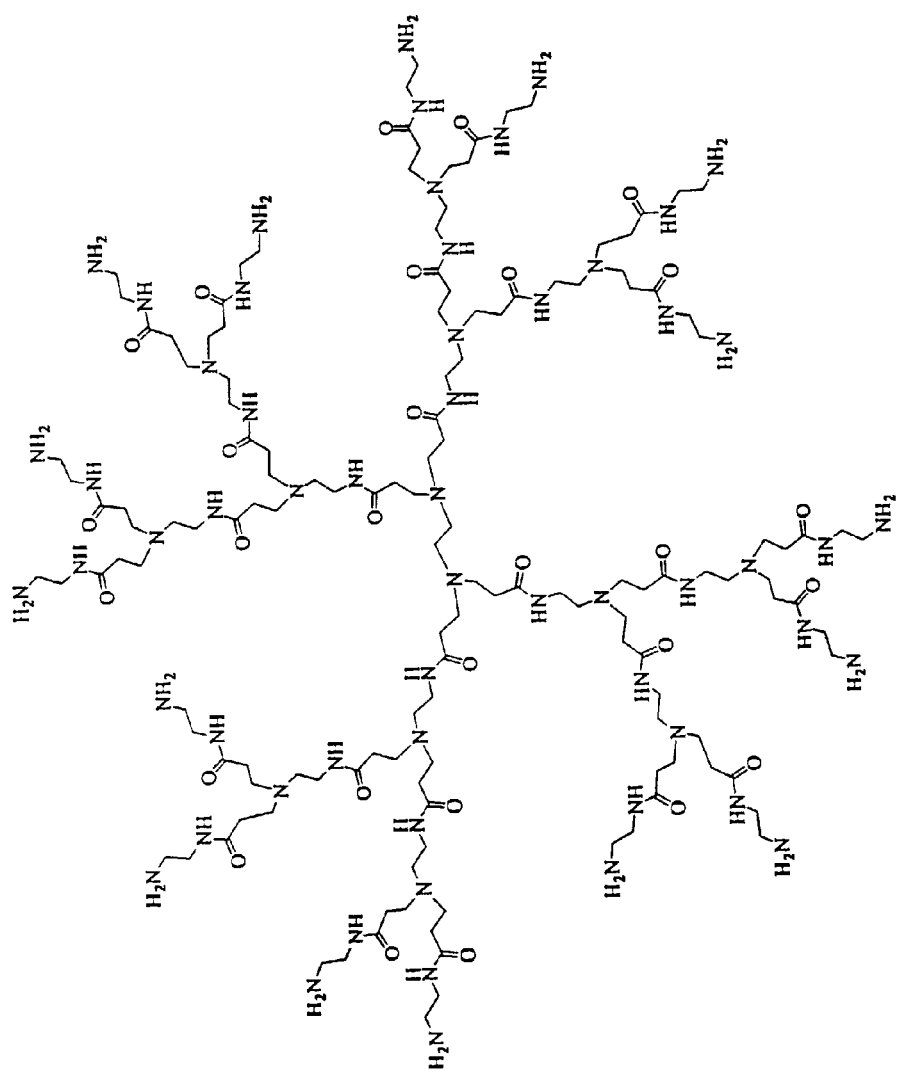

FIG. 2d shows the structure of a polar, hydrophilic dendrimer, which is well known as the commercially available Starburst® PAMAM (Polyamidoamine) dendrimer (Dendritech, Inc.). The structure shown in FIG. 2d is a generation-2 dendrimer. The core of the structure is derived from ethylenediaminetetrapropionic acid and thus has four arms, which serve to bind the repeating units through amide bonds. The repeating units are derived from 1,2-diaminoethane and propionic acid, which are again linked with each other through amide bonds. The linker units at the surface are provided by the amino groups of the outer shell of the repeating units. Therefore, no spacer units can be assigned in this case. However, it is noted that PAMAM-dendrimers are commercially available with amino, carboxylate, or hydroxy surface groups, which can directly be used as linker units. In order to improve binding of the dendrimer to the other component(s) of the composite material, it is also possible to utilize the surface groups for attaching spacer units and linker units which may be better suited for cross-linking the material.

Figure 2E:
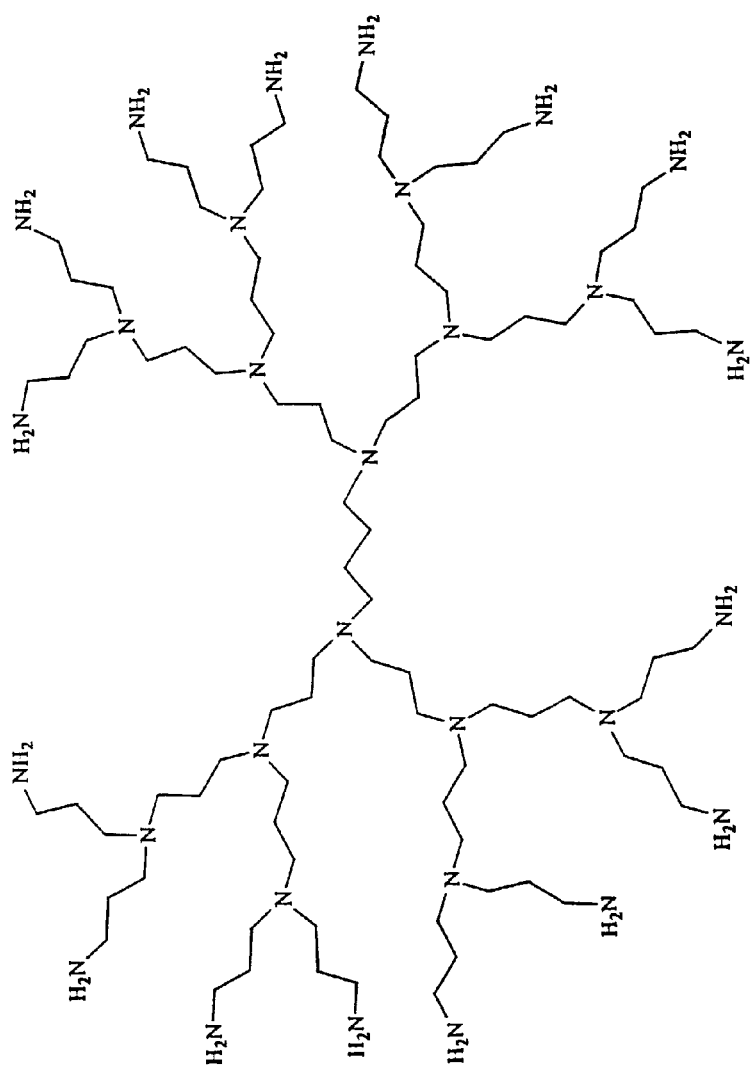

Also the dendrimer shown in FIG. 2e is commercially available (Sigma-Aldrich) as DAB-Am-16, Polypropylenimine hexadecaamin dendrimer, which is also referred to as poly(propylene imine)-, or PPI-dendrimer. The core of this structure is derived from 1,4-diaminobutane and has, therefore, four arms, which are the valences of the nitrogen atoms. The repeating units are aminopropyl units. The structure shown in the figure has three shells of repeating units and is therefore a generation-3 dendrimer. Also in this example the linker units are provided by the amino groups of the repeating units, which form the outer shell. Therefore, no spacer units can be assigned. However, the surface amino groups may be utilized to attach other spacer and linker units, which may be better suited for cross-linking the composite material.

In both dendrimer structures, which are shown in FIG. 2d and FIG. 2e, the branching positions are nitrogen atoms. Both structures are pretty flexible, since the structural units comprise a high content of $sp^3$-hybridized atoms with a high degree of conformational freedom. Since in both cases the structure contains amide- or amine-groups these dendrimers are suited for the fabrication of sensors with selectivity for polar, hydrophilic analytes. Hydrophilic amide groups contained in PAMAM-dendrimers can act as endo-receptors and therefore enhance the selectivity towards polar analytes. Because of their amine functional groups PPI-dendrimers are especially selective to acidic analytes.

FIG. 3 shows a chemiresistor, which has a nanoparticle film as a sensitive element. On a substrate 6 are placed interdigitated electrodes 7. On the substrate 6 is deposited a composite film 8, which covers the electrode structures 7.

A constant current may be applied to the leads 9 of the electrodes and a change in the voltage across the electrodes may be detected by a detector (not shown). The detailed part of the figure shows the nanoparticles 10 interlinked through dendrimer molecules 11 thereby forming a dendrimer/nanoparticle network.

Nanoparticle preparation

Figure 4A:
FIG. 4a shows a TEM micrograph of Au-nanoparticles used for assembling the sensor film.
Figure 4B:
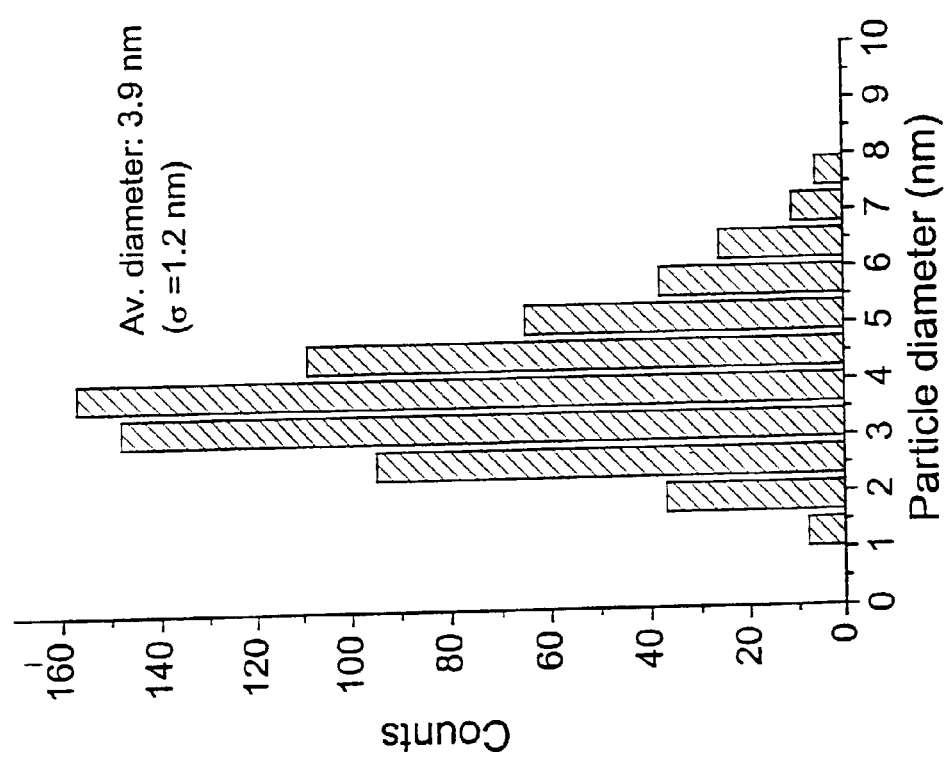

A wet-chemical method previously described by Leff et al., Langmuir 1996, 12, 4723-4730, was used to prepare a colloidal solution of dodecylamine-stabilized Au-nanoparticles. To a rapidly stirred solution of 160 mg AuCl$_3$ in 20 ml water a solution of 639 mg tetraoctylammoniumbromide in 20 ml toluene was added. It was stirred until the organic phase turned into red-orange, while the aqueous phase turned colourless. To the mixture 1178 mg dodecylamine and 30 ml toluene were added. Under vigorous stirring a freshly prepared solution of 221 mg NaBH$_4$ in 15 ml water was added. The colour of the solution immediately turned into deep purple. After stirring over night under ambient conditions the organic phase was separated and 40 ml ethanol were added. The mixture was stored in the freezer at −18° C. over night. By filtration through a nylon membrane (0,45 µm pore size) the precipitate was separated from the solution and redissolved in about 20 ml toluene. This solution was subjected to fractionated precipitation, which was done by repeating the following three steps: 1. Addition of ethanol (ca. 40 ml), 2. Letting sit over night in a freezer, 3. Separation of the precipitate by centrifugation or filtration. This way four fractions were obtained, from which fraction 2 was used for sensor fabrication. TEM analysis of fraction 2 revealed that the Au-nanoparticles were crystalline and had an average diameter of 3.9 nm with a standard deviation of 1.2 nm. A TEM micrograph is shown in FIG. 4a. Counting 700 particles gave the size distribution visualized in FIG. 4b. In contrast to alkanethiol stabilized Au-particles these amine-stabilized particles easily undergo ligand-exchange reactions and are therefore well suited as building blocks for the facile layer-by-layer assembly of nanoparticle/dendrimer films. The interaction of a gold surface with amino groups is much weaker than with thiol groups. Therefore thiol or disulfide functionalized dendrimers can easily exchange alkylamine ligands on the nanoparticle surface. However, as will be shown below, also amino-functionalized dendrimers can exchange the alkylamine ligands on the nanoparticle surface. The relatively weak stabilization of the Au-particles by dodecylamine also accounts for the broad size-distribution observed even after fractionated precipitation. A broad size distribution however is not necessarily a disadvantage for sensing applications. Since a broad size distribution enhances the porosity of the composite material it supports the diffusion of analyte within the film, and thereby may improve its sensitivity.

Figure 5A:
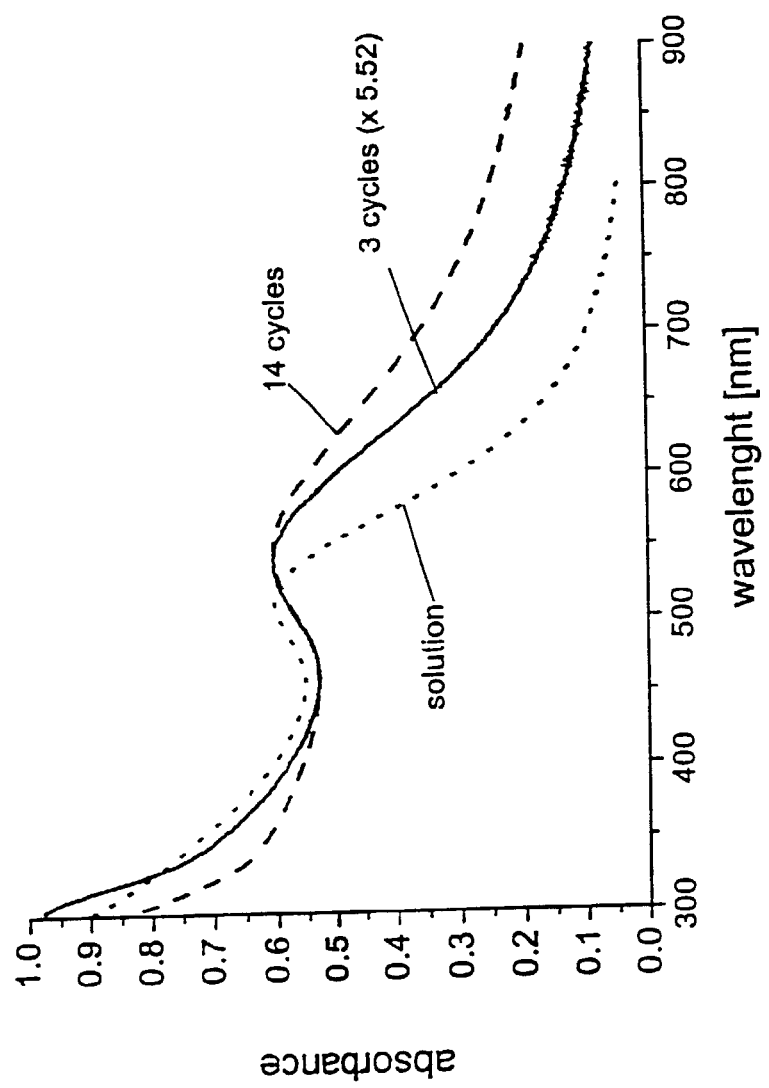
FIG. 5a shows the UV/vis spectra of an Au-nanoparticle solution and the spectra of a polyphenylene-dendrimer/Au-nanoparticle film after 3 and 14 deposition cycles.
Figure 5B:
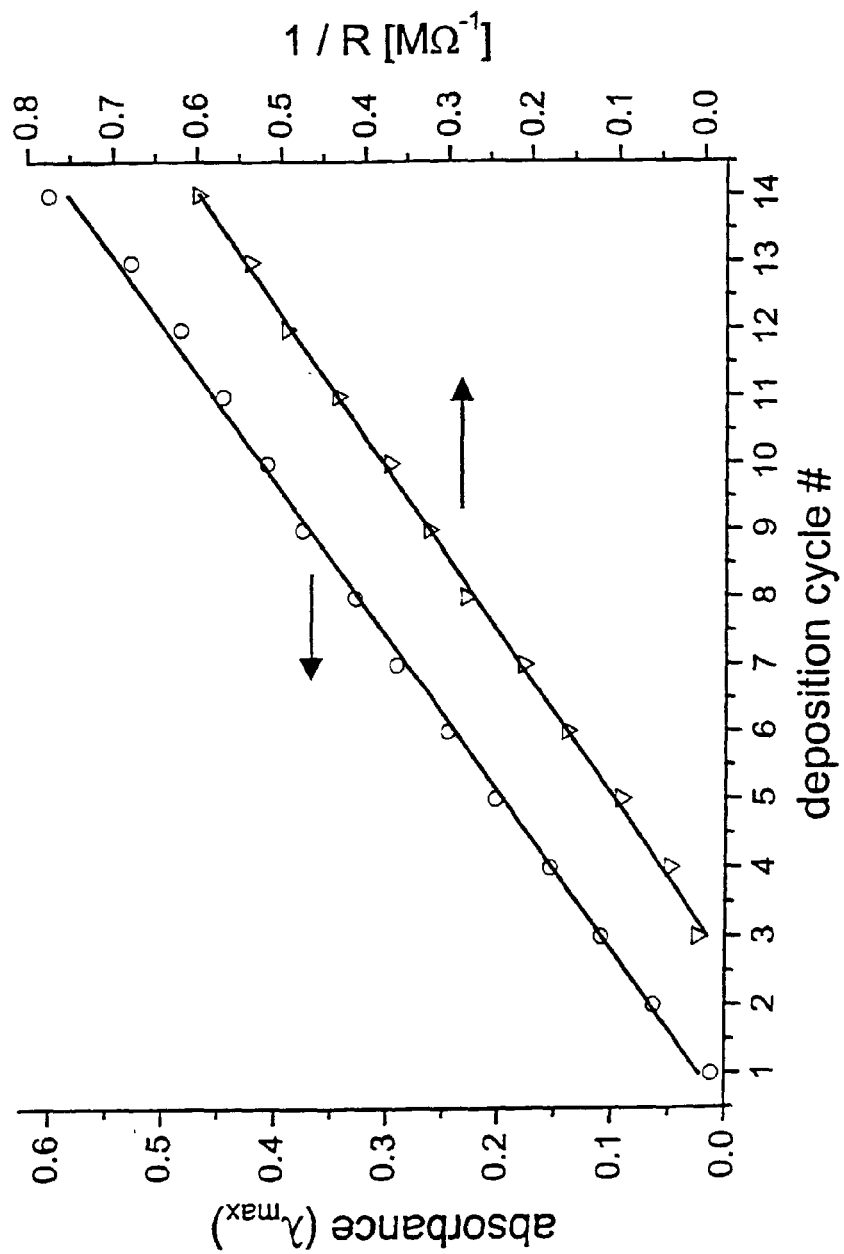
FIG. 5b shows the increase of the plasmon absorption (at $\lambda_{max} \approx 550$ nm) and the conductance increase during stepwise growth of a polyphenylene-dendrimer/Au-nanoparticle film.
Figure 6A:
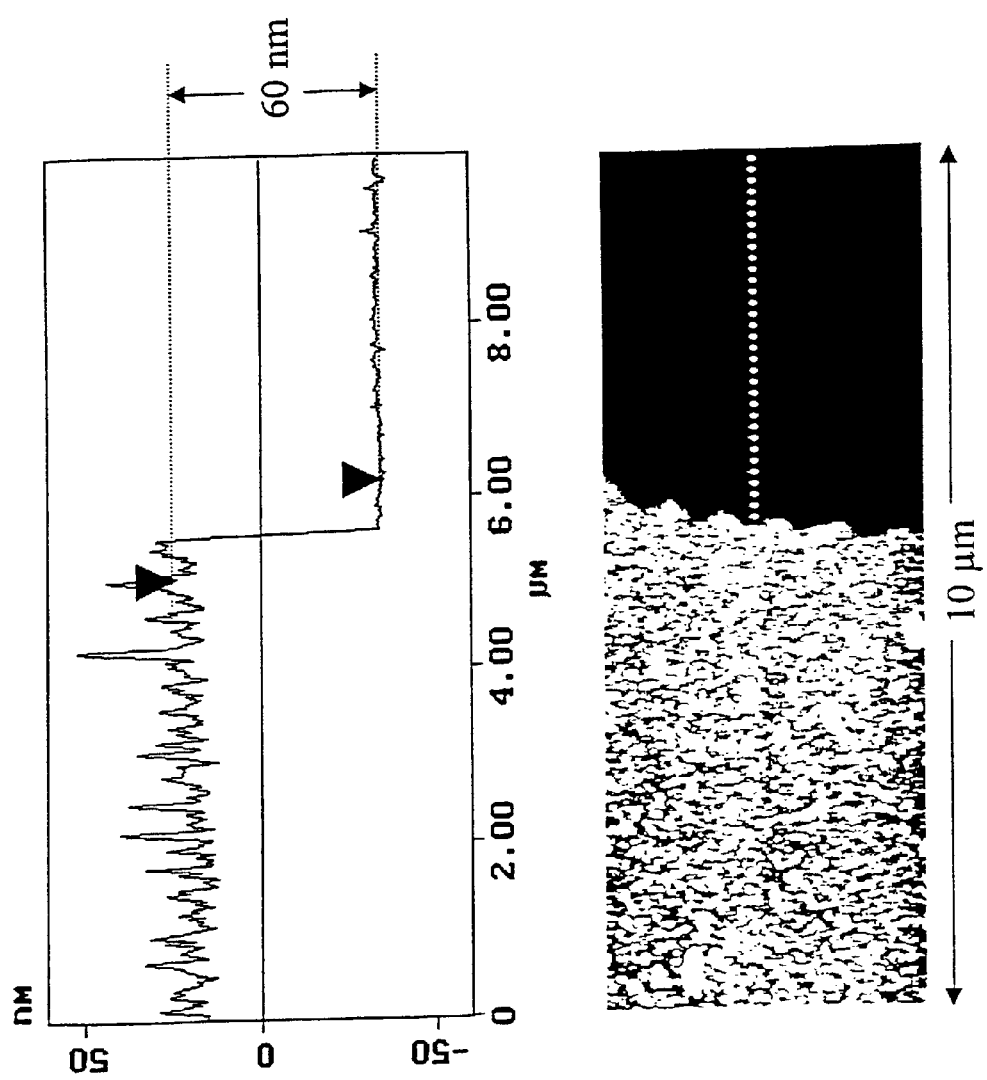
FIG. 6a shows an AFM image of a polyphenylene-dendrimer/Au-nanoparticle film according to the invention at the edge of a scratch (bottom part); the top part shows a profile scan across the edge of the film.
Figure 6B:
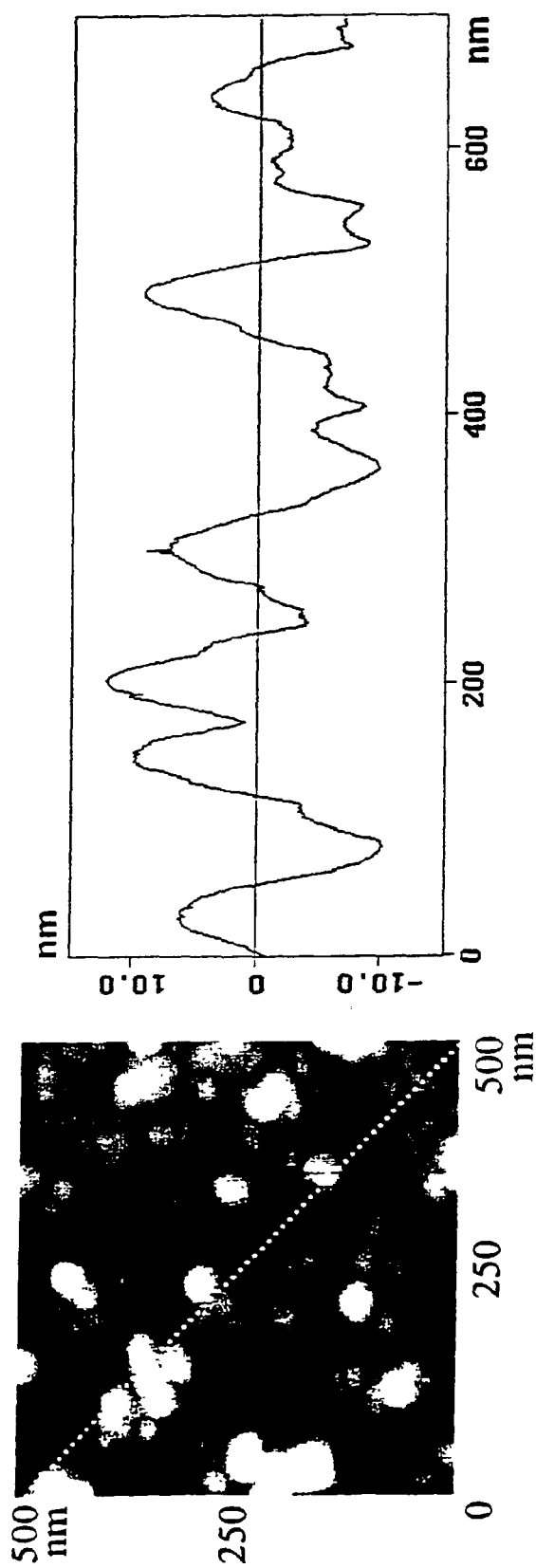
FIG. 6b shows an AFM image of the film displayed in FIG. 6a at higher magnification and a profile scan.

Fabrication and characterization of an electrically addressable polyphenylene-dendrimer/Au-nanoparticle composite film:

For assembling a sensor film a dendrimer having a structure as depicted in FIG. 2a (R=thioctic acid residue) was used. The film was deposited onto BK7 glass substrates supporting lithographically made interdigitated electrode structures. The electrode structures comprised a 5 nm titanium adhesion layer on which a 95 nm gold layer was deposited. They comprised 50 finger pairs having a width of 10 µm, a spacing of 10 µm, and an overlap of 1800 µm. Before assembling the sensor film, the substrates were cleaned in an ultrasonic bath with acetone, hexane, and isopropanol and by applying an oxygen plasma (4 min. at 30 W and 0.24 mbar). The cleaned substrates were immersed into a solution of 50 µL 3-aminopropyldimethylethoxysilane in 5 mL toluene and heated to 60° C. for 30 minutes. This procedure functionalized the glass substrates with amino groups, which served as linking groups for subsequent nanoparticle deposition. After washing the functionalized substrates with toluene they were exposed for 15 minutes to a toluene solution containing dodecylamine stabilized Au-nanoparticles. The concentration of the Au-nanoparticles corresponded to an absorption of 0.4 at $\lambda_{max}$=514 nm (10 mm path length). Next, the substrates were rinsed with solvents and then exposed to the linker solution, which contained 10 mg dendrimer of the formula shown in FIG. 2a (R=thioctic acid residue) in a mixture of 5 mL toluene and 300 µL dichloromethane. After exposing the substrates for 15 minutes to the linker solution they were rinsed with toluene. Then the procedure of exposing the substrates to nanoparticle solution and linker solution was repeated 14 times. Accordingly, the final treatment, which provided the uppermost layer of the film structure, was done by applying the dendrimer solution. In between the deposition cycles the substrates were dried in a nitrogen stream and the UV/vis spectra (using a Varian Cary 50 Scan spectrometer) and resistances were measured. FIG. 5a shows the UV/vis spectra of an Au-nanoparticle solution and the spectra of the composite film after 3 and 14 deposition cycles. As seen, the plasmon absorption band of the film ($\lambda$=550 nm) is redshifted, when compared to the solution phase spectrum (λ=514 nm). This phenomenon has been observed before (T. Vossmeyer, E. DeIonno, J. R. Heath, *Angew. Chem. Int. Ed. Engl.* 1997, 36, 1080) and can be explained in terms of the different dielectric environment and particle-particle interactions in case of the film material. However, as also seen in the figure the maximum of the absorption band of a 3-layered film is approximately at the same position as the one of the 14-layer film. This indicates that during successive film growth the average particle-particle interaction is not significantly changed. Such a behavior is typical for films comprising large linker molecules (M. D. Musick et al., *Chem. Mater.* 2000, 12, 2869-2881). FIG. 5b shows how the plasmon absorption (at $\lambda_{max}$≈550 nm) and the conductance increase during film growth. The linear increase of both, the absorption and the conductance, indicate that during each assembly cycle the same amount of Au-nanoparticles is deposited. It is noted that during the first few weeks after film preparation we observed an increase of the film's resistance (1.6 MΩ-5.7 MΩ). The electronic transport properties of the film were investigated by IV-measurements at variable temperature using a home-built setup comprising a liquid nitrogen container, a computer interfaced temperature controller and a HP4142B Source/Monitor unit. At room temperature, IV-measurements displayed ohmic behavior within the range of +/−3 V, corresponding to a field of +/−3 kVcm$^{-1}$. Only at higher fields and at low temperatures (<200 K) we observed slight deviation from linear behavior. The temperature dependence of the conductance was measured between 250 and 100 K and at a field of 0.5 kVcm$^{-1}$. We observed that ln(1/R) decreased linearly with increasing 1/T, which is consistent with an Arrhenius type activation of charge transport according to $\sigma \propto \exp(-E_a/kT)$, where σ is the conductivity (see for example: C. A. Neugebauer, M. B. Webb, *J. Appl. Phys.* 1962, 33, 74-82). From the slope of an ln(1/R) vs 1/T plot we determined the activation energy $E_a$ as 78 meV, which is in agreement with theoretical considerations and with results reported by others (see for example: B. Abeles, P. Sheng, M. D. Coutts, Y. Arie, *Adv. Phys.* 1975, 24, 407-461; M. Brust, D. Bethell, D. J. Schiffrin, C. J. Kiely, *Adv. Mater.* 1995, 7, 795-797). In order to characterize the film thickness as well as the film topography we used tapping-mode atomic force microscopy (AFM). The bottom part of FIG. 6a shows an AFM image of the film at the edge of a scratch. The step-profile across the edge in the top-part of the figure reveals that the film is about 60 nm thick, which is about 10 nm less than expected for dense packing of a multilayered structure comprising spheres of 3.9 nm and 2.5 nm in diameter. This observation indicates that each deposition step does not lead to the formation of a complete monolayer of the respective component. Taking into account the actual film thickness, the geometry of the interdigitated electrode structures and the resistance of the film, we calculated the room temperature conductivity of the composite material to be around 5.5×10$^{-6}$Ω$^{-1}$cm$^{-1}$. The profile-scan in the top part of FIG. 6a also reveals that the film structure is quite rough when compared to the smooth surface of the BK7-glass substrate. This indicates that the film material is highly porous. FIG. 6b shows an AFM image of the film at higher magnification. It shows that the dendrimers and nanoparticles aggregate into small beads. Due to the tip-convolution it is difficult to estimate the size of the aggregates. However, the profile scan on the right hand side of the figure suggests that the beads have a size on the order of tens of nanometer. This means that the beads consist of only a few to tens of Au-nanoparticles and dendrimers.

Fabrication of electrically addressable PAMAM-dendrimer/Au-nanoparticle and PPI-dendrimer/Au-nanoparticle films:

Similar as described above, we prepared PAMAM- and PPI-dendrimer/Au-nanoparticle composite films. As the only differences we used solutions of 10 mg PAMAM-G4 (generation-4) or PPI-G3 (generation-3) dendrimers in 5 ml methanol instead of the polyphenylene dendrimer solution.

Figure 7A:
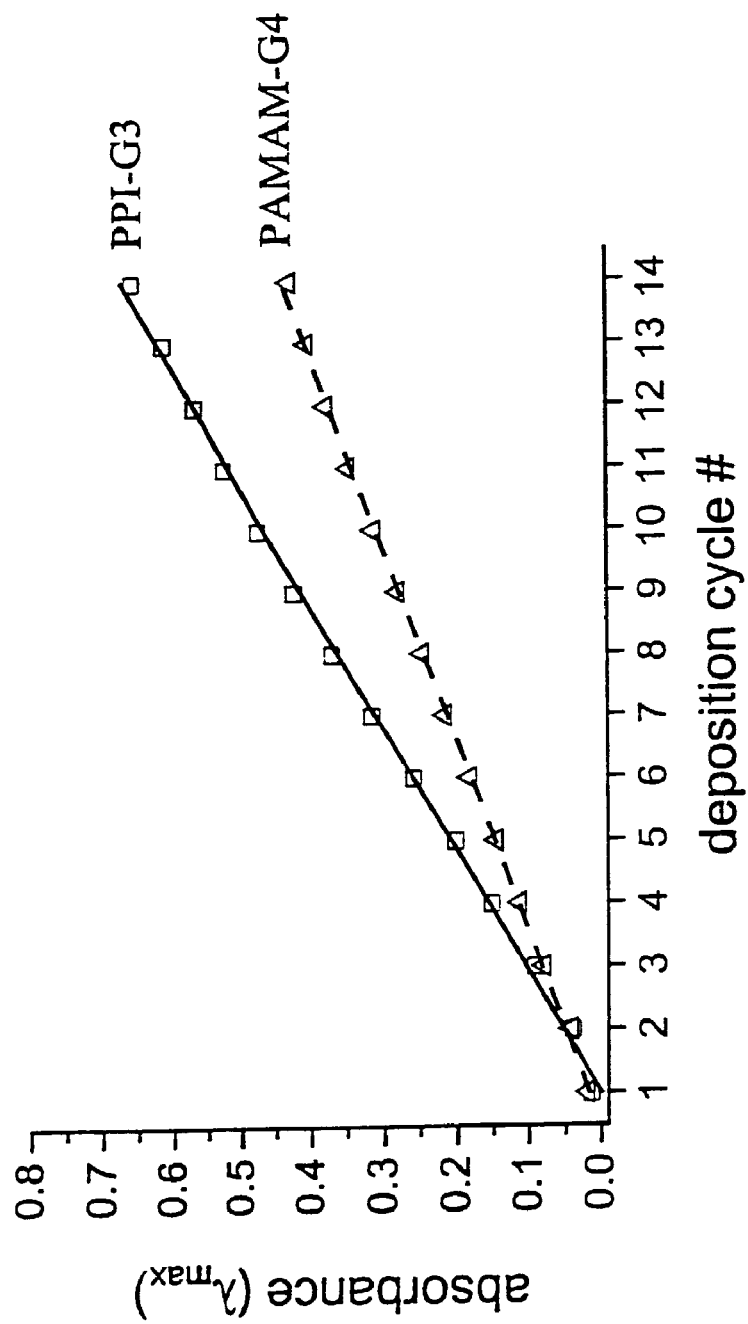
FIG. 7a shows the increase of the plasmon absorption (at $\lambda_{max} \approx 526\text{-}560$ nm) during the stepwise assembly of a PPI-dendrimer/Au-nanoparticle film and a PAMAM-dendrimer/Au-nanoparticle film.
Figure 7B:
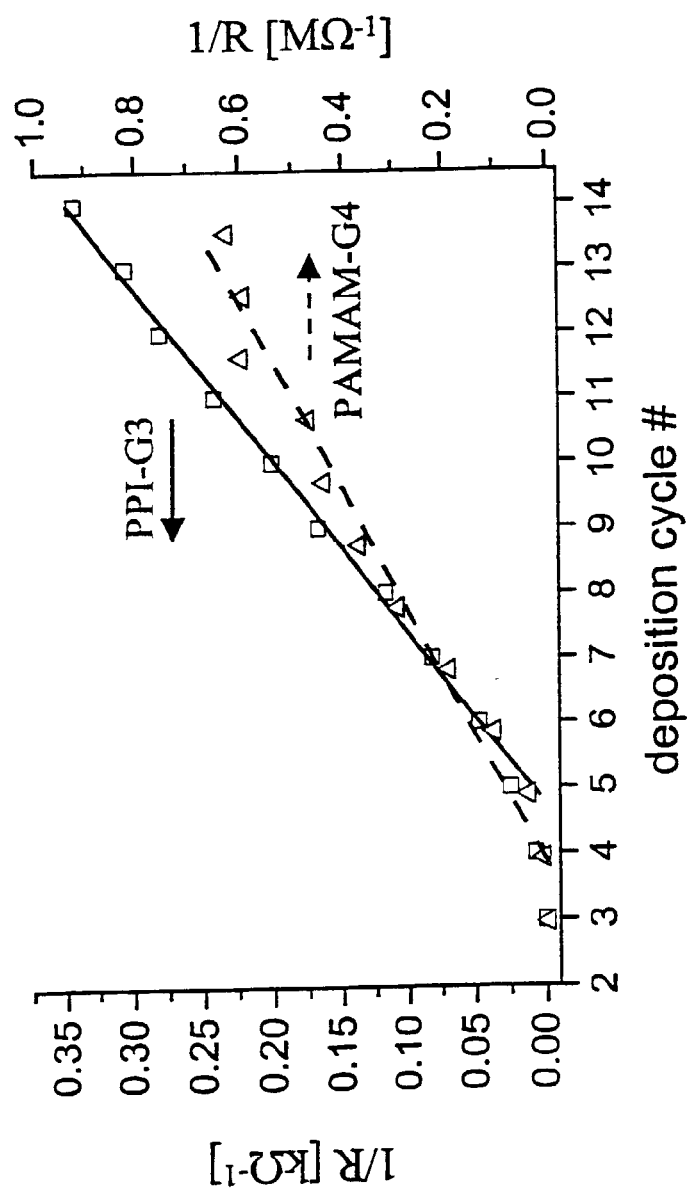
FIG. 7b shows the increase of conductance during the stepwise assembly of a PPI-dendrimer/Au-nanoparticle film and a PAMAM-dendrimer/Au-nanoparticle film.

After each exposure of the substrates to the dendrimer solutions, the substrates were first rinsed with methanol and then with toluene, before exposing them to the Au-nanoparticle solutions. Accordingly, after exposing the substrates to the nanoparticle solutions, they were first rinsed with toluene and then with methanol before exposure to the dendrimer solutions. It is noted that the PAMAM- and PPI-dendrimers we used comprised 64 and 16 primary surface amino groups, respectively, which served as linker units to cross-link the Au-nanoparticles. FIG. 7a shows how the maximum values of the Au-nanoparticles' plasmon absorption ($\lambda_{max}$≈526-560 nm) increase during stepwise film deposition. The linear increase of the plasmon absorption again indicates that during each deposition cycle about the same amount of Au-nanoparticles is deposited. However, it is seen that when using the PPI-dendrimers more Au-nanoparticles are deposited than in the case of the PAMAM-dendrimers. One possible explanation for this result may be the fact that the molar concentration of the PPI-dendrimer solution, which was used for film deposition, was around 8 times higher than in the case of the PAMAM-dendrimer solution. Therefore the PPI-dendrimer solution may have replaced the dodecylamine ligands on the Au-nanoparticles' surfaces more efficiently. FIG. 7b shows the increase of conduction measured after each deposition cycle. It is seen that the deposition cycles 3 to 5 leads to a comparable low increase of conductance. This may be due to "island" formation and lateral growth of such islands until the substrate surface is completely covered with a thin film of the Au-nanoparticle/dendrimer composite material. After the first five deposition cycles, the conductance of the PPI-dendrimer/Au-nanoparticle film increases linearly, which indicates highly reproducible deposition of the film's components. However, in the case of the PAMAM-dendrimer composite material, the measured values of the conductance are more scattered, but also increase during stepwise film deposition. After 14 deposition cycles, the PAMAM-dendrimer/Au-nanoparticle film had a resistance of 1.5 MΩ, whereas the PPI-dendrimer/Au-nanoparticle film had a resistance of 3.0 kΩ. The higher resistance of the former material is explained by its higher organic-to-metal ratio, which is due to the relative low Au-content and the much larger size of the PAMAM-dendrimers ($M_r$=14215 g mol$^{-1}$), when compared to the PPI-dendrimers ($M_r$=1687 g mol$^{-1}$).

Figure 8:
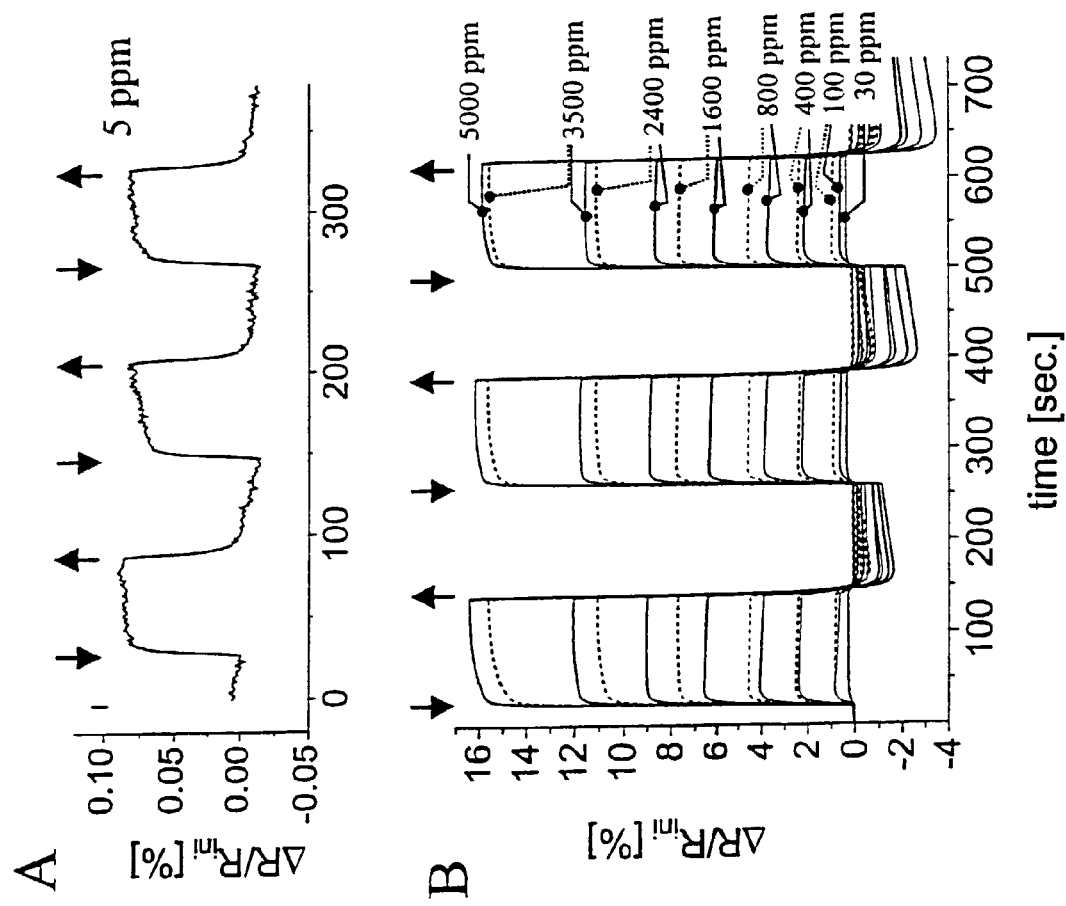
FIG. 8 shows responses of a polyphenylene-dendrimer/Au-nanoparticle composite thin film resistor to exposure with toluene vapor.
Figure 9:
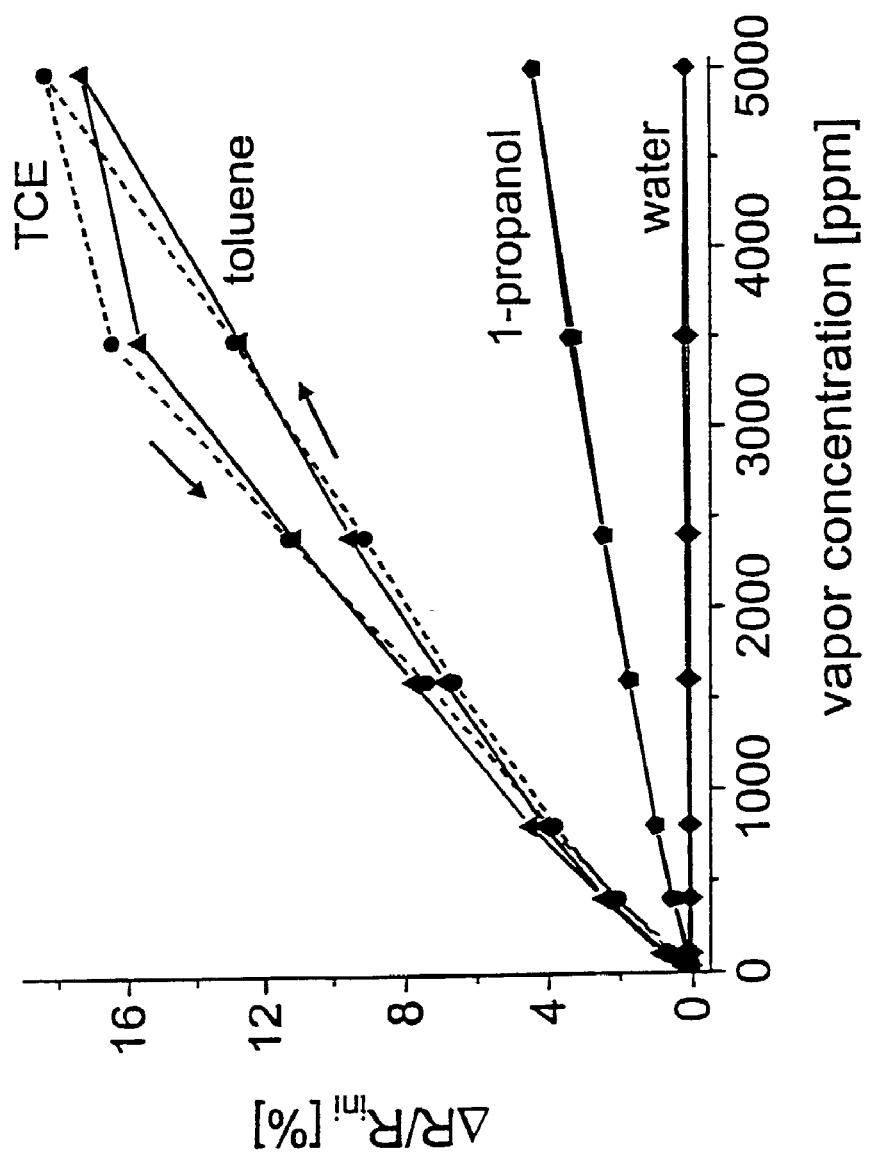
FIG. 9 shows the sensitivity isotherms of a polyphenylene-dendrimer/Au-nanoparticle sensor film measured by dosing the sensor with various vapors.

Vapor sensing properties of the polyphenylene-dendrimer/Au-nanoparticle film:

FIG. 8 shows the typical responses of an Au-nanoparticle/dendrimer composite thin film resistor to exposure with toluene vapor. Arrows down indicate switching from dry, purified air to toluene vapor atmosphere, whereas arrows up indicate switching back to air. The solid curves were measured in direction of increasing concentration (30 ppm to 5000 ppm), whereas the dashed curves were measured in direction of decreasing concentrations (3500 ppm to 30 ppm) (see also FIG. 9). During the measurements the film was kept at 39° C. because this was found to improve the reversibility of the response when using the sensor over prolonged time periods (i.e. weeks). As seen in the figure the sensor device responded with an increase of resistance to the exposure with toluene vapor. Figure part A shows that the sensor responded well resolved even to very low vapor concentrations (5 ppm). The sensor response was fast ($t_{90}$ <5 sec.) and reversible. At higher concentration (figure part B) a decrease of resistance was observed, when switching from toluene atmosphere back to air. This decrease of resistance became stronger at higher concentrations and when repeating the exposure to toluene. Without being bound to theory, this observation suggests that there are at least two opposing components making up the total response of the sensor. One component increases the resistance and dominates the sensor signal during exposure to test gas. This component has a fast recovery, when switching back to air. The other component decreases the resistance and has a slow recovery, when switching back to air. We may qualitatively explain the increase of resistance as being due to a swelling of the film material, which causes an increase of the average particle distance, whereas the decrease of resistance may be due to diffusion of analyte molecules into open voids of the film material. The latter process may increase the dielectric constant of the material without changing the average particle distance. Thus, this component would decrease the film's resistance. It is noted that open voids, which can take up solvent molecules, are especially provided by the dendrimer's rigid interior structure formed by the polyphenylene repeating units. The structural part of the dendrimer, which is able to swell and thus to increase the inter-particle distances is the shell of spacer units, which comprises flexible alkyl chains. FIG. 9 shows the sensitivity isotherms measured by dosing the sensor with various vapors. As seen the response to hydrophobic analytes toluene and tetrachloroethylene (TCE) is much stronger than towards the more hydrophilic 1-propanol or towards water itself. This result can be understood by the hydrophobic nature of the polyphenylene dendrimer structure. It is also seen that the isotherms recorded with toluene and TCE show hysteresis. This hysteresis is caused by the response behavior, which was already discussed above (see FIG. 8). It seems that exposure to vapor, especially at high concentration, increases the sensitivity by decreasing the "baseline resistance" as indicated by FIG. 8. In FIG. 10 we compare the sensitivities, which were measured with a polyphenylene-dendrimer/Au-nanoparticle based chemiresistor and a nonanedithiol/Au-nanoparticle based chemiresistor. The latter was fabricated as described above but by using 5 μL nonanedithiol instead of the dendrimer. The comparison shows that the sensitivity of the dendrimer comprising chemiresistor is almost one order of magnitude higher than that of the nonanedithiol inter-linked one. Since in both cases a hydrophobic cross-linker was used for sensor fabrication the sensitivity is higher for the non-polar vapors.

Comparison of the vapor-sensing properties of a polyphenylene-dendrimer/Au-nanoparticle film resitor, a PAMAM-dendrimer/Au-nanoparticle film resistor, and a PPI-dendrimer/Au-nanoparticle film resistor:

FIG. 11 shows the response curves of a polyphenylene-dendrimer/Au-nanoparticle film resistor (A), a PAMAM-dendrimer/Au-nanoparticle film resistor (B), and a PPI-dendrimer/Au-nanoparticle film resistor (C) to the exposure of 5000 ppm toluene, 1-propanol, and water. As already seen from FIG. 9, the polyphenylene-dendrimer/Au-nanoparticle film resistor shows strong response to the non-polar toluene vapor, weaker response to the more polar 1-propanol vapor and only very little response to water. As mentioned above, this result is expected because of the hydrophobic nature of the dendrimer structure. In stark contrast, the film comprising PAMAM-dendrimers shows a complementary sensitivity pattern. Toluene gives almost no response, 1-propanol gives a clearly stronger response, and water gives the strongest response, which is about two orders of magnitude higher than that for toluene. This result is also expected because of the hydrophilic nature of the PAMAM-dendrimers. The sensor film comprising the PPI-dendrimers shows a higher sensitivity for toluene and 1-propanol and a lower sensitivity for water vapor, when compared to the responses of the PAMAM-dendrimer/Au-nanoparticle film. Compared to both other sensor films, the response towards toluene and 1-propanol is much slower and is still far from reaching equilibrium after 2 minutes exposure. Taken together, the sensitivity patterns of the three different sensor films clearly illustrate that the chemical selectivity of chemical sensors made from such composite materials can be controlled by the chemical nature of the dendrimer component.

Equipment used for sensor characterization:

The vapor-sensing properties of the Au-nanoparticle/dendrimer composite films were investigated by exposing the film to various solvent vapors while measuring the change of resistance as the sensors' signal. For dosing the sensors with the test vapors, we used a gold plated aluminum chamber, equipped with pogo pin contacts pressing onto the contact pads of the electrode structures. The chamber was equipped with a meandering heat-exchange channel for thermally equilibrating the test vapors. Since we observed that operating the sensors at elevated temperatures improved the sensors' recovery after vapor exposure, we kept the temperature of the test chamber constant at 39° C. in all experiments. Moreover, in order to remove contaminants from the sensor's surfaces the devices were kept in vacuum (ca 8 mbar) for about six hours before each experimental run. Usually the sensors were operated by applying a constant direct current (using a Keithley Source-Measure-Unit 236) and measuring the change of voltage across the electrodes (using a Keithley 2002 Multimeter) while applying a test gas atmosphere. The sensors were operated at a bias below 1V. Vapors of solvents were generated with commercial gas calibration systems (Kalibriersystem MK15/MK5 or MK15-DDS-RL/MK5, Umwelttechnik MCZ GmbH, Ober-Mörlen, Germany). These systems comprise bubblers and condensers for preparing saturated solvent vapors in a temperature range between 15 to 50° C. By using several mass flow controllers the saturated vapors were diluted with zero-gas to a concentration range of 1 to 5000 ppm (ppm=volume parts per million). As zero gas we used purified and dried air (dew point −70° C.), which was provided by a commercial zero-gas generator (Nullgasanlage MD2000-25, Umwelttechnik MCZ), equipped with a catalytic purification unit. The mass flow system was equipped with a computer-controlled valve for switching the gas flow through the sensor cell between zero-gas and test gas. As test-gas vapors we used toluene, tetrachloroethylene (TCE), 1-propanol, and water. The actual concentrations of the vapors in the test cell were calculated by using the Antoine equation and the dilution factors adjusted by the mass flow system. The mass flow in the test chamber was adjusted to 400 mL/min and kept constant for all experiments.

The invention claimed is:
1. A chemical sensor, comprising:
 a substrate having a surface;
 a sensor medium formed on the substrate; and
 a detection means for detecting a change of a physical property of the sensor medium, wherein the sensor medium comprises a network formed of non-linear polymer or oligomer molecules having linker units and of particles of at least one second component, wherein the linker units are bound to the surface of the particles of the at least one second component thereby interlinking the particles, wherein the particles of the at least one second component are nanoparticles, wherein the nanoparticles consist of a metal, and wherein the chemical sensor is exposed to an analyte and a change of a physical property of the sensor film is measured by detection, wherein the change of the physical property is a change of the electronic transport properties.

2. The chemical sensor according to claim 1, wherein the non-linear polymer or oligomer molecule is a dendrimer molecule.

3. The chemical sensor according to claim 2, wherein the dendrimer molecules comprise an interior formed of a core and a shell of branched repeating units, and an outer shell of linker units.

4. The chemical sensor according to claim 1, wherein the linker units are formed by polar groups.

5. The chemical sensor according to claim 1 wherein the linker unit comprises a sulphur-containing group.

6. The chemical sensor according to claim 4, wherein the linker unit is selected from a group consisting of disulfide group, thiol group, thiolate group, isocyanate group, thiocarbamate group, dithiocarbamate group, sulfonium group, and amino group.

7. The chemical sensor according to claim 3, wherein at least 40% of the carbon atoms of the core and the shell of branched repeating units are $sp_2$ or sp hybridized.

8. The chemical sensor according to claim 3, wherein the dendrimer core and/or the shell of branched repeating units comprise at least one structural unit, selected from the group consisting of adamantane, cyclodextrin, crown ether, porphyrin, and phthalocyanine.

9. The chemical sensor according to claim 3, wherein the core and/or the shell of branched repeating units comprise polar endo-receptor sites.

10. The chemical sensor according to claim 3, wherein the dendrimer molecule is a polyamidoamine (PAMAM) dendrimer.

11. The chemical sensor according to claim 2, wherein the dendrimer molecule is a poly(propylene imine) (PPI) dendrimer.

12. The chemical sensor according to claim 3, wherein the core and/or the shell of branched repeating units comprise electron-donating groups, which are complexed with metal cations.

13. The chemical sensor according to claim 3, wherein the interior of the dendrimer molecule has a hydrophobic structure.

14. The chemical sensor according to claim 13, wherein the hydrophobic structure is formed by a polyphenylene structure or comprises phenylene units.

15. The chemical sensor according to claim 2, wherein the dendrimer molecule is a metallodendrimer.

16. The chemical sensor according to claim 2, wherein the shell of linker units is connected to the shell of branched repeating units by a shell of spacer units.

17. Chemical sensor according to claim 16, wherein the spacer units have a flexible structure comprising alkylene chains which comprise at least three carbon atoms.

18. The chemical sensor according to claim 1, wherein the metal is selected from the group consisting of Au, Ag, Pt, Pd, Co, Cu, Ni, Cr, Mo, Zr, Nb, Fe, or any combination of those metals.

19. The chemical sensor according to claim 1, wherein the chemical sensor is formed as a chemical sensitive resistor, a chemical sensitive transistor, a chemical sensitive diode, or a chemical sensitive capacitor.

20. The chemical sensor according to claim 1, wherein the surface of the substrate is functionalized in order to provide linker groups on the surface of the substrate.

21. A chemical sensor, comprising:
a substrate having a surface;
a sensor medium formed on the substrate; and
a detection means for detecting a change of a physical property of the sensor medium,
wherein the sensor medium comprises a network formed of non-linear polymer or oligomer molecules having linker units and of particles of at least one second component,
wherein the linker units are bound to the surface of the particles of the at least one second component thereby interlinking the particles,
wherein the dendrimer molecules comprise an interior formed of a core and a shell of branched repeating units, and an outer shell of linker units, and
wherein the dendrimer core and/or the shell of branched repeating units comprise at least one structural unit, selected from the group consisting of adamantane, cyclodextrin, crown ether, porphyrin, and phthalocyanine.

* * * * *